United States Patent
Regimand

[19]
[11] Patent Number: 5,923,726
[45] Date of Patent: Jul. 13, 1999

[54] VALIDATION AND CALIBRATION APPARATUS AND METHOD FOR NUCLEAR DENSITY GAUGES

[75] Inventor: Ali Regimand, Raleigh, N.C.

[73] Assignee: InstroTek, Inc., Raleigh, N.C.

[21] Appl. No.: 08/873,815

[22] Filed: Jun. 12, 1997

[51] Int. Cl.$^6$ .................................................. G06F 15/52
[52] U.S. Cl. .............................. 378/207; 378/56; 378/89; 250/252.1
[58] Field of Search .................................. 378/53, 54, 56, 378/86, 88, 89, 90, 207; 250/252.1, 390.01, 390.04

[56] References Cited

U.S. PATENT DOCUMENTS

| | | | |
|---|---|---|---|
| 4,152,600 | 5/1979 | Berry | 250/252.1 |
| 4,587,623 | 5/1986 | Regimand et al. | 364/571 |
| 4,791,656 | 12/1988 | Pratt, Jr. et al. | 378/89 |

OTHER PUBLICATIONS

CPN brochure, MC–3 Portaprobe, believed to be prior art No date.
CPN brochure, Model MC1DR, believed to be prior art No date.
CPN Manual, pp. 24–27, MC–3 Portaprobe, believed to be prior art No date.
Humboldt brochure and related manual pp. 2–4, 7, 62–74, Humboldt HS–5001–C Nuclear Compaction Control Gage, believed to be prior art No date.
Troxler brochure and related manual pp. 4–7 through 4–11, The Troxler 3440, believed to be prior art No date.
ASTM D2922, Density of Soil and Soil–Aggregate in Place by Nuclear Methods, pp. 268–274, believed to be prior art No date.
ASTM D2950, Density of Bituminous Concrete in Place by Nuclear Methods, pp. 257–260, 1991.
Williamson, T.G. et al.; Laboratory and Field Evaluation of the Nuclear Moisture and Density Meters; Purdue Univ.; Joint Highway Research Project (PB169908); (Feb. 11, 1966).

(List continued on next page.)

*Primary Examiner*—David P. Porta
*Attorney, Agent, or Firm*—Myers Bigel Sibley & Sajovec, P.A.

[57] ABSTRACT

A cost effective, field-usable validation and calibration apparatus and method for nuclear density gauges comprises an absorption element, where absorption element is capable of simulating at least one known density when subjected to analysis using the nuclear density gauge. The absorption element may be positioned inside an enclosure, which also may include an insertion hole capable of receiving a source rod from a nuclear density gauge. The absorption element also can be capable of simulating a plurality of densities, both in backscatter and direct transmission modes. A method of validating and re-calibrating a nuclear density test gauge is also provided, where only a single block of a known density, either a reference block or a field block with a simulated density, is required.

43 Claims, 13 Drawing Sheets

OTHER PUBLICATIONS

Smith, T. et al.; Calibration Standards for Nuclear Gages (Density Standards); California State Div. of Highways, Materials and Research Dept. (PB189354); (Nov. 1969).

Obermuller, J.C. et al.; Relative Compaction Study; California State Div. of Highways. Materials and Research Dept. (PB203740); (Mar. 1971).

Webster, S. L., Determination of In–place Moisture and Density by Nuclear Methods; U.S. Army Engineer Waterways Experiment Station Vicksburg, Miss (AD779422); (Apr. 1974).

Castanon, D.R. et al.; Calibration Standards for Nuclear Gages—Density and Moisture Standards; California State Dept. of Transportation (PB253170); (Dec. 1975).

Benson, P.E. et al.; Precision of the Relative Compaction Test Using Nuclear Gages; California State Dept. of Transportation, Sacramento Transportation Lab (PB268098); (Dec. 1976).

Wyant, D. C.; Implementation of Nuclear Gage Moisture Standards; Virginia Highway and Transportation Research Council, Charlottesville (PB275737); (Dec. 1976).

Nuclear Gauges for Measuring the Density of Roadbase Macadam: Report of a Working Party, Transport and Road Research Lab. (PB83232934); Crowthorne, England (1982).

LeFevre, E. W.; Determination of the Correlation Between Nuclear Moisture/Density Tests and Standard Tests on Certain Gravel Bases in South Arkansas; Arkansas University; Dept. of Civil Engineering (PB86175072); (1984).

Tidwell, L.E. et al.; Evaluation of Surface Density Nuclear Gauges for Acceptance Testing of Asphalt Concrete Overlays; Army Engineer Waterways Experiment Station, Vicksburg, MS. Geotechnical Lab (ADA269887); (Sep. 1993).

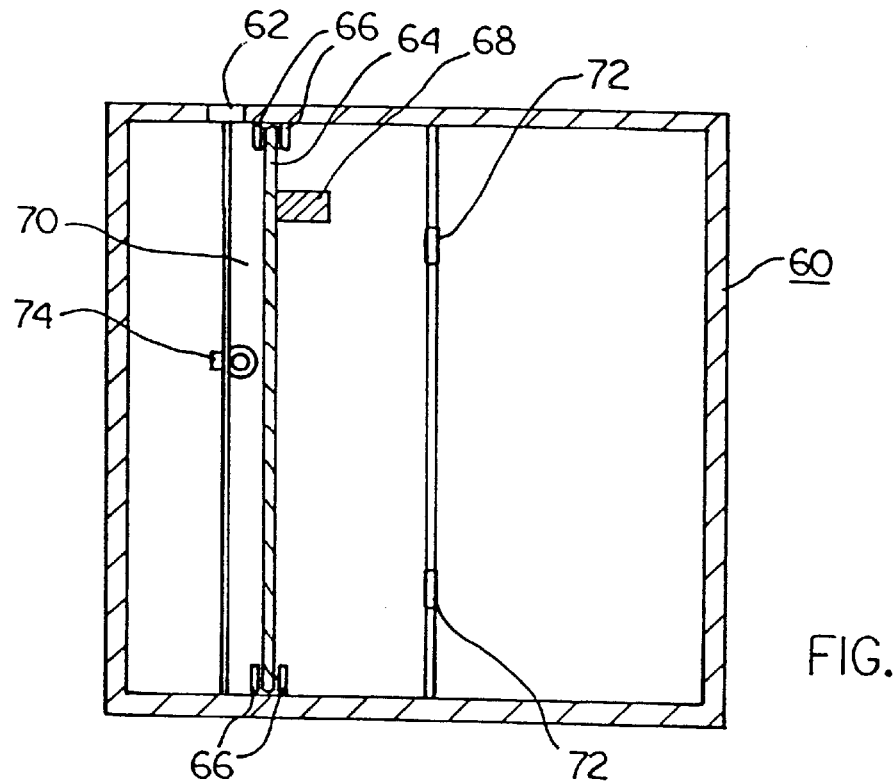
FIG. 6A
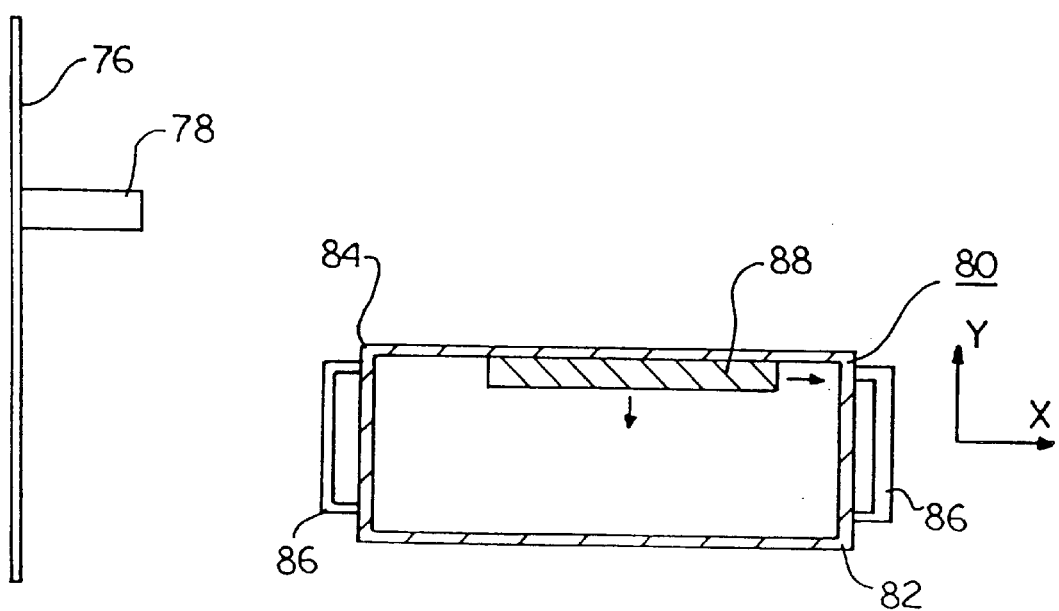
FIG. 6B
FIG. 7

VALIDATION AND CALIBRATION APPARATUS AND METHOD FOR NUCLEAR DENSITY GAUGES

FIELD OF THE INVENTION

The present invention generally relates to nuclear density gauges and more specifically to an improved field usable validation and calibration apparatus and for nuclear density gauges.

BACKGROUND

Compaction measurement is of great significance in the construction of highways, airports, railway embankments, trench backfills, dams and foundations. The knowledge of material density can be a major indicator of how well a resident structure will perform its intended usage. Under compaction can cause serious deformation and settlement of the structure, while over compaction can cause cracks that affect the required material strength. Also, in-place density measurements are necessary to ensure proper testing of asphalt paving used in highways, airports and parking lots. Either by design choice or to comply with standards and/or job requirements, density measurements are used as a field quality control test for monitoring the compaction of soil, asphalt and concrete structures.

Nuclear gauges are the standard method of density measurement in most heavy construction projects. Various State Departments Of Transportation (DOT), as well as the Federal Highway Administration (FHWA), have adopted specifications for use of nuclear density gauges. Nuclear gauges are used to determine compliance with the specification for construction projects. While, there are numerous testing methodologies in use to measure structure density, nuclear testing devices are the preferred standard around the world, due to their speed, accuracy, and convenience.

Older, more primitive testing methods such as sand cone (soils), balloon (soils) and core samples (asphalt) testing are time-consuming and involve taking samples of the test materials off-site for analysis. Results are often not available for as long as 24 hours after sampling, which is especially problematic in asphalt construction projects. These testing processes are labor-intensive and necessarily involve the destruction of small pieces of the structure material. Nuclear gauges, on the other hand, are portable devices which are placed on the material and automatically display the material density in as little as 15 seconds.

Nuclear Density Gauge Theory

Nuclear density gauges operate by using a very small radioactive source and a detection system. When placed on the test material, the photons from the nuclear source penetrate the material. A fraction of the photons will interact with the material and scatter to the gauge base where they are detected by Geiger Mueller detectors. The number of photons scattered back and counted by the detectors is proportional to the material density.

Nuclear gauges can operate in two different modes: backscatter and direct transmission. In the backscatter mode, the gauge is placed on the test material with the source and the detectors in the same plane. The photons from the source penetrate the material from the surface and scatter to the detectors. This mode is normally used for measurement of asphalt and hardened concrete. Hence, no destruction of the test structure occurs. In the direct transmission mode, a hole larger than the diameter of the source rod is formed in the material (normally soils) and the source is inserted into the material at a predetermined depth. In this mode, the material is located directly in the path between the source and the detectors.

Nuclear density gauges are also widely used in the processing industry for measurement of raw material density and automatic control of process operations. Even though the design of the radioactive source material and detectors are different than the ones used in the construction industry, the principles of density measurement are the same as discussed above. Therefore, the teachings of this invention can be used for the calibration validation and calibration of nuclear density devices in all other industries.

Calibration of Nuclear Gauges

As with many testing instruments, calibration is of vital importance for nuclear gauges. Presently, nuclear gauges are calibrated in the factory by using blocks of known density. These blocks are large (i.e. 24" L, 17" W, 14" H) and heavy (360 to 560 lbs). The blocks often consist of metals (i.e. magnesium, aluminum, and/or a combination block of magnesium and aluminum) and natural materials such as limestone and granite. Gauges are placed on these blocks and a "count" is obtained at each depth. Gauge measurements may involve counts obtained at depths of 0 inches (backscatter) to 12 inches (direct transmission), as well as intermediate depths at increments of 0.5, 1 or 2 inches, depending on the gauge design. These counts, along with the known block densities, are used in an equation such as $$CR = A\, e^{(-BD)} - C \qquad (1)$$

where:

CR is a count ratio or ratio of gauge count on the test material and a standard count A, B and C are gauge parameters for each depth D is the material density The standard count is collected with the gauge on a small polyethylene block provided with each gauge. The standard count corrects the gauge counts for source decay (i.e. approximately 2.4% each year for Cesium-137) and minor electronic drift. The constants A, B and C are determined by a suitable curve fitting process using mathematical and computer methods well known in the art. These values are entered into the gauge memory for calculation of density in the field. Thus, each gauge receives values for the constants A, B and C for each depth from the factory calibration process.

Field Density Measurements

In the field, a count reading is taken on a test material. This reading is used, along with the A, B, and C constants for each depth and the standard count, to calculate a density using the rearranged equation (1) from above:

$$D = \frac{1}{B} * \ln\left(\frac{A}{CR + C}\right) \qquad (2)$$

Calibration Standards and Requirements

Two ASTM standards that currently require validation of the nuclear gauge calibration are as follows: ASTM standard D2922, "Density Of Soil and Soil-Aggregate In Place By Nuclear Methods (Shallow Depth)" and ASTM Standard D2950, "Standard Test Method For Density Of Bituminous Concrete In Place By Nuclear Methods." ASTM D2922, requires that nuclear gauge calibration be verified at least once every 12–18 months. ASTM D2950 requires a verification of gauge calibration at least once per year. While the standards set forth the intervals for calibration and verification, there is little instruction on how and with what type of device the verification can be performed.

Nuclear gauges are calibrated with large and expensive density standards before leaving the factory. Each manufacturer uses a slightly different calibration method. The calibration is performed to establish the count to density relationship for each unit produced. Calibration enables the gauge to measure field material density.

Gauges are typically used in a very rough construction environment. Presently, two questions are commonly raised regarding the gauge calibration validity. The first question concerns how long a gauge will operate without a need for new calibration. The second question concerns the possible variation in density measurements of two gauges on a given material. The two gauges can be of the same make and model, or from different manufacturers. Without a reliable validation device, it is impossible to determine if one or both gauges require a new calibration. The answer to these questions presently can only be obtained by returning the gauges to the manufacturer or other testing laboratories equipped with calibration standards for verification and calibration of the gauges at all depths of operation. In addition to the costs charged by such entities to perform the new calibration (in effect, a re-calibration), the shipping costs and loss of use (an average of two weeks) can be substantial as well. Therefore, because of the inconveniences of the calibration techniques used today, users and manufacturers have yet to be provided with suitable tools to answer the question of whether and how often their gauge needs calibration. Thus, the absence of suitable validation and calibration techniques have hindered users who desire feedback that they are getting consistent and accurate results.

A small number of gauge owners have used two methods for gauge calibration validation. Some have molded blocks out of concrete for validation purposes. However, blocks made from construction materials are heavy and cannot be transported easily from site to site. Also, the block density can change, due to wear and the degree of moisture absorption over time. This change in block density defeats the usefulness of these blocks, since they cannot be relied on as a fixed density reference to validate the gauge calibration. Also, in some instances, a fixed location is marked on concrete floors or asphalt parking lots for gauge validation. Gauges are placed on this spot from time to time to test the validity of the calibration. The measurements under this condition are affected by the change in the material density over time and limited to the backscatter mode only. Also, validation at one depth cannot be used to predict accurately gauge calibration validity at other depths.

Prior art methods of calibration include those described in U.S. Pat. Nos. 4,587,623 and 4,791,656. U.S. Pat. No. 4,587,623, of which applicant is a co-inventor, uses the constant B from the original factory calibration and actual gauge counts on the magnesium and aluminum standard block to calculate the parameters A and C of equation (1) above. In this process, curve fitting is not necessary. The block densities, the B parameter and the counts can be plugged into the calibration equation and A and C are analytically calculated. The two blocks used for performing this calibration are large, heavy, expensive and not portable.

U.S. Pat. No. 4,791,656, requires the purchase of three blocks. Namely a magnesium block, a magnesium/ aluminum (Mg/Al) combination block and an aluminum block. This method relies on the counts obtained from the Mg/Al combination block and historical relationships developed between Mg/Al and magnesium, and Mg/Al and aluminum blocks, of known densities to calculate counts for magnesium and aluminum, at all depths. These three counts are then used with an appropriate fitting routine to determine the parameters A, B and C. The method in the '656 patent requires an initial purchase of three blocks and a collection of data for a predetermined period. The data collected is then used to develop linear relationships between Mg/Al and magnesium, and Mg/Al and aluminum. After a determination of these historical relationships, this method provides an efficient calibration method for the gauge manufacturer. However, it is not a field practical and cost effective solution for the gauge users due to the requirement of multiple reference blocks.

Gauge users need a convenient and portable validation block that can be used as a fixed density reference and one that does not change with time. Also, if it is shown that the calibration cannot be validated, it is desirable to have a simple calibration process so that gauges can be calibrated, without the costly and cumbersome processes of shipping the gauge off-site for calibration.

SUMMARY OF THE INVENTION

A cost effective, field-usable validation and calibration apparatus and method for nuclear density gauges are provided. The apparatus comprises an absorption element, where the absorption element is capable of simulating at least one known density when subjected to analysis using the nuclear density gauge. The absorption element may be positioned inside an enclosure, which also may include an insertion hole capable of receiving a source rod from a nuclear density gauge. The absorption element also can be capable of simulating a plurality of densities, both in backscatter and direct transmission modes. A method of validating and re-calibrating a nuclear density test gauge is also provided, where only a single block of a known density, either a reference block or a field block with a simulated density, is required.

The apparatus and the method described herein provides the industry with a uniform validation method and a calibration method. It will also serve as a field standardization method for gauge density readings taken on a given material for all gauge models regardless of the manufacturer.

These and other aspects of the present invention as disclosed herein will become apparent to those skilled in the art after a reading of the following description of the preferred embodiments when considered with the drawings.

BRIEF DESCRIPTION OF THE DRAWINGS

FIG. 6A is a cross-section of yet another embodiment of this invention.

FIG. 6B illustrates an absorption element according to another embodiment of this invention.

The drawings are for the purpose of describing a preferred embodiment of the invention and are not intended to limit the present invention.

DESCRIPTION OF THE PREFERRED EMBODIMENTS

Figure 1:
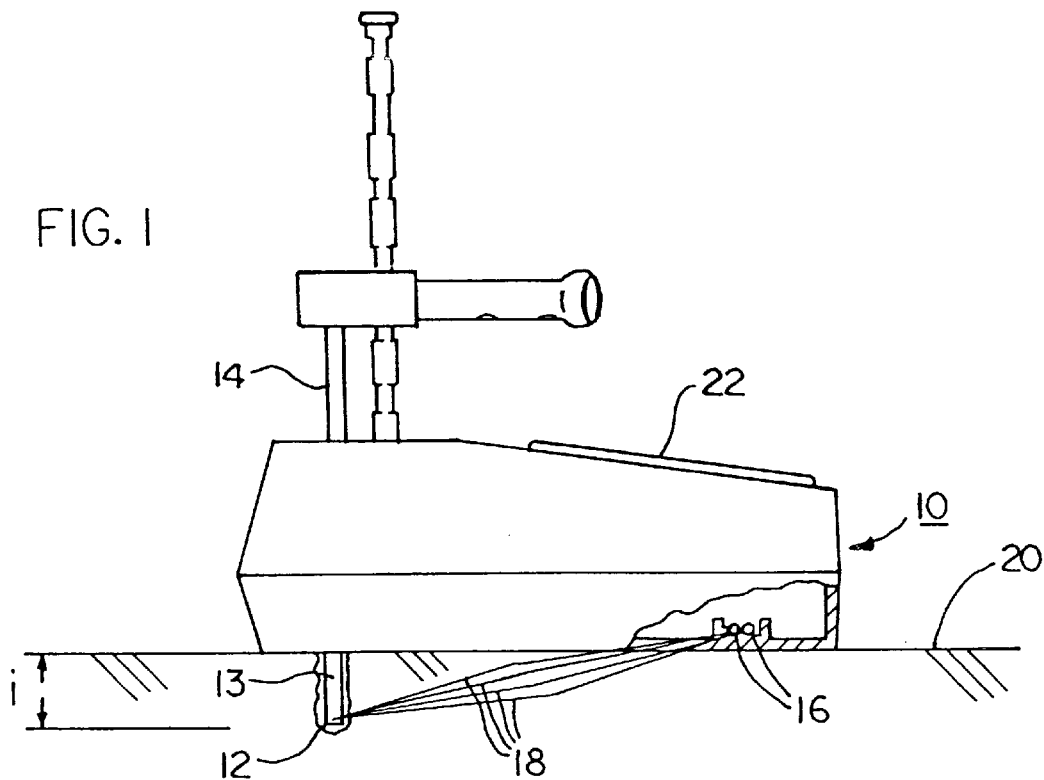
FIG. 1 is an elevation view (with partial cut-away) of a nuclear gauge tester.

FIG. 1 shows a representative nuclear gauge 10. Manufacturers of such gauges include: Humboldt Scientific, Inc. of Raleigh, N.C.; Campbell Pacific Nuclear (CPN) of Martinez, Calif.; Troxler Electronic Laboratories, Inc., of Research Triangle Park, N.C.; and Seaman Nuclear of Milwaukee, Wis. As is well known in this art, a nuclear gauge 10 operates by using a small radioactive source 12 (e.g., Cesium-137) positioned in a source rod 14. Detectors 16 (e.g., Geiger Mueller) are mounted in the base of the gauge as shown. The measurements can be taken from the surface to a depth (i) of 12 inches, and at increments therebetween (e.g., 1 inch increments).

Surface measurements, where i is zero, are referred to as "backscatter." In this mode, the source and the detectors are in the same plane separated by a fixed distance. At depths other than at the surface, such measurements are known as "direct transmission." Thus, "direct transmission" occurs when the source rod is inserted into the test material at depths (i) varying from, for example, 2" to 12" from the surface. The parameters and measurements for each depth are different and must be determined independently.

During testing, a nuclear density gauge is placed on the material 20 sought to be tested. For direct transmission tests, a bore 13 is formed in the material 20 for the insertion of the source rod 14. The radioactive source in the source rod emits photons, which penetrate the material. Photons from the nuclear source interact with the material and a fraction will scatter to the detectors 16 in the gauge base. Representative photon paths 18 are shown in FIG. 1. Electronics and a display 22 capable of performing calculations are also contained within the gauge.

The number of photons scattered back to the detectors is proportional to the material density. In the density range (approximately 1600 kg/m3 to 2700 kg/m3) of construction materials, the higher the material density the lower the detected counting rate of the gauge.

Figure 2:
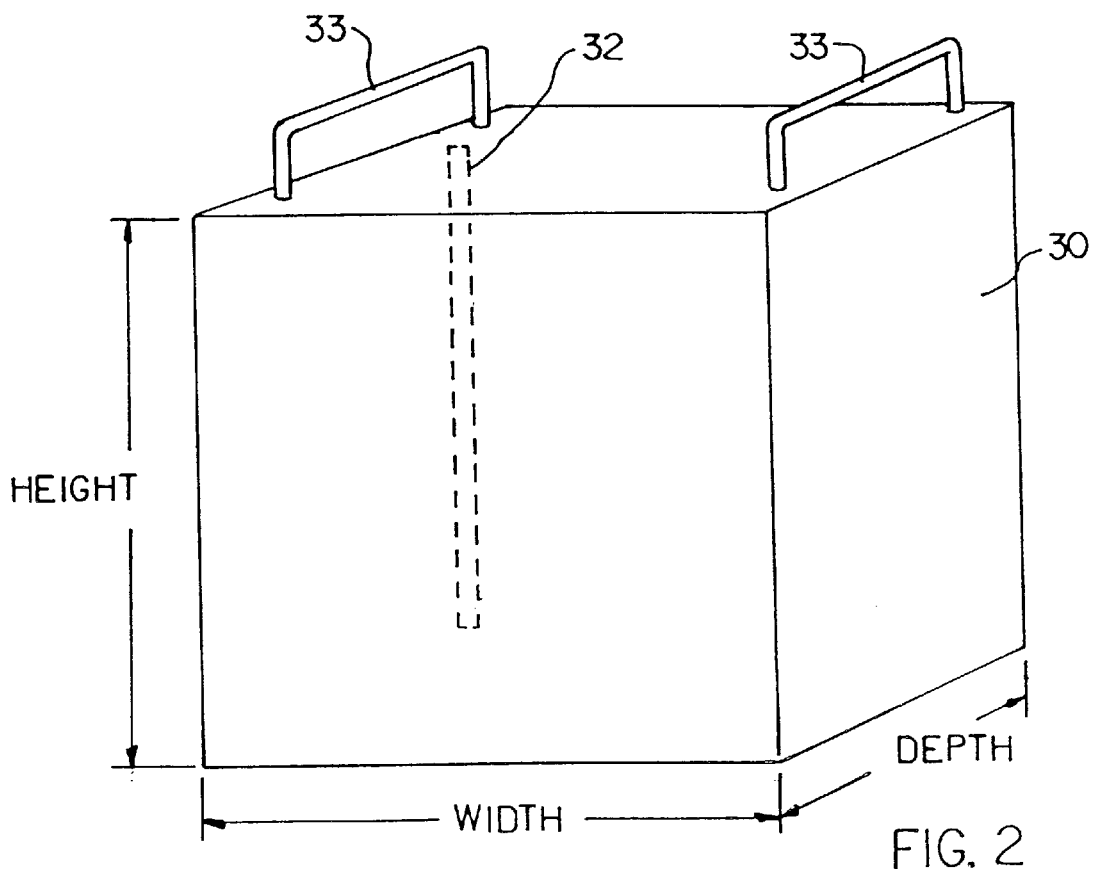
FIG. 2 is an isometric view of a validation and calibration field test block according to this invention.

FIG. 2 depicts one embodiment of a representative portable, light weight, in-field calibration and verification block 30 (hereinafter may be referred to as "field block") according to this invention. In a preferred embodiment, the field block is approximately 10" in width, 14" in length, and 14" in depth. However, the shape of the block is not limited to the shape shown. Other block configurations with different dimensions and geometrical shapes can also be used with different design and operating modes of the gauge that will allow this invention to be practiced as well. Carrying handles 33, or other suitable means to allow for easy movement, also are provided for the operator to lift and transport the unit to and from the field. Other means for transporting the field block include carrying straps, handles formed within the walls of the block, separate carrying case or bag, carrying cart, casters designed into the block, integrated handle and wheel design, and the like.

An insertion tube 32 can be positioned in the top of the block, extending downward into the block. In a preferred embodiment, the tube 32 has a diameter of approximately 1" and is located approximately 2" in from one edge of the block. An insertion tube 32 is not required if the field block is intended for use only in backscatter modes. For this type of an embodiment, the overall dimensions can be different, e.g., 16 inches length by 10 inches width and 5 inches in height.

Figure 3:
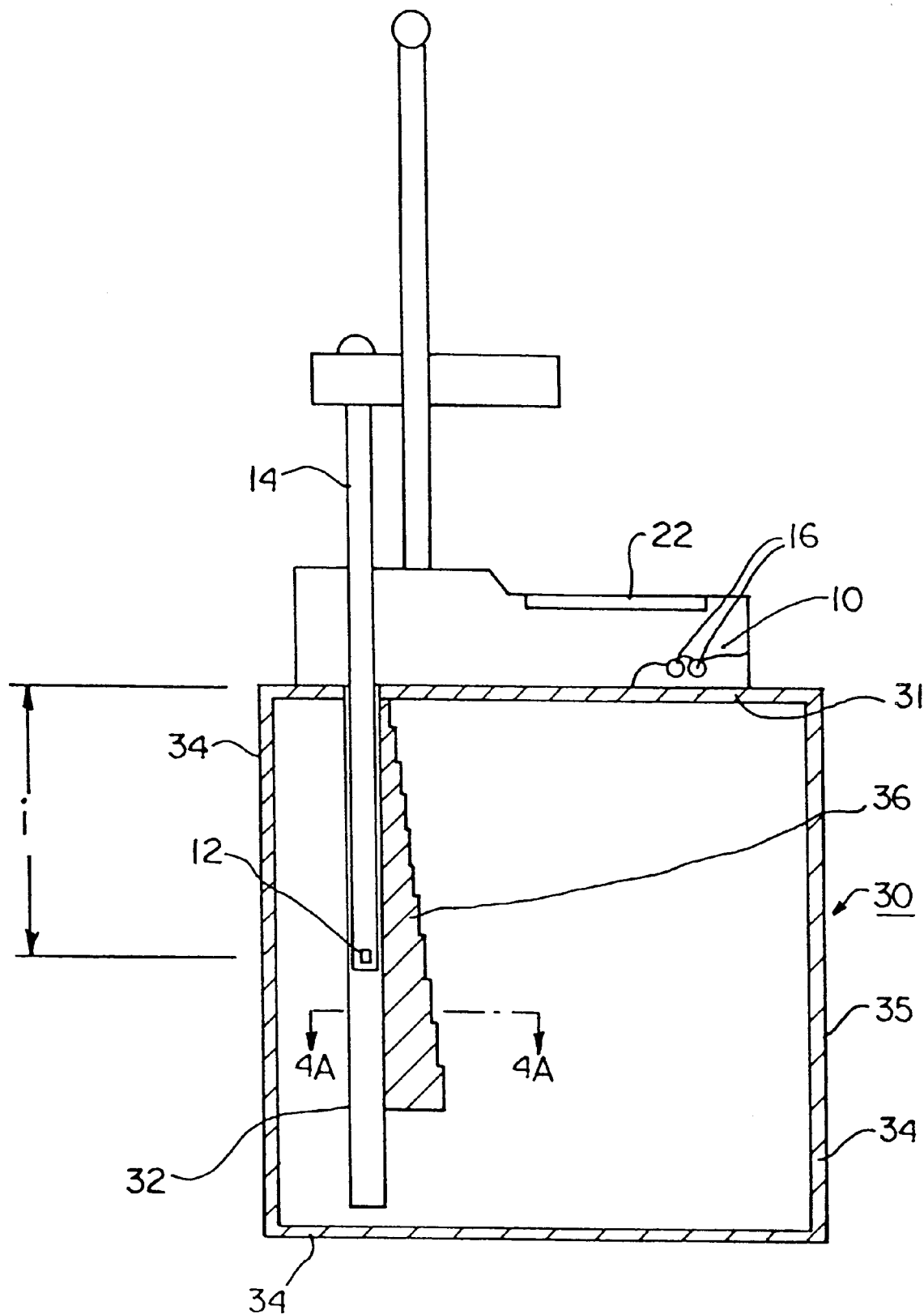
FIG. 3 is a cross-section view of a validation and calibration field test block and nuclear gauge.

FIG. 3 shows a cross-sectional view of a field block 30 according to one embodiment of this invention. Lead or other suitable bottom and side shielding liner 34 is placed within the walls 35 of the block. An absorption element 36, constructed of lead or other suitable material, is positioned inside the block within the radiation path of the gauge to simulate one or more fixed densities at different depths i. Top liner 31 serves the dual purpose of shielding the user from radiation, as well as acts as an absorber, which will influence the ability of the block to simulate densities. Using this construction, density ranges of standard construction materials (1600 to 2700 kg/m3) can be achieved by placing varying amounts of lead or other material in the radiation path of the gauge. In this manner, blocks of any desired density can be simulated.

In a preferred embodiment, the field block 30 comprises an enclosure, such as an aluminum sheet metal (1/8" thick) hollow enclosure, with a length of 14", width of 10", and height of 14". This block can be wrapped on the inside or outside of all surfaces of the enclosure with a 0.005" layer of lead sheet 34 for shielding the gauge operator from the nuclear source. In addition to aluminum, those skilled in the art will realize that the enclosure can be designed from plastic sheets, Plexiglas, molded material, wood or other materials suitable for field and laboratory use.

The block 30 can have an insertion tube 32 with a diameter of 1" to accommodate positioning the source rod at different depths in the enclosure. A 1.25" by 1.25" lead absorption element 36 with a thickness varying from 0.1" to 7" can be positioned adjacent the insertion tube 32, in the radiation path, at different depths. Those skilled in the art understand that other materials with high density such as Tungsten, Cadmium, etc., can be used. Moreover, it is not necessary that the absorption element 36 be comprised of the same material; combinations of materials can be used as well. The absorption element 36 is placed in the radiation path between the source 12 and detectors 16 to create blocks that would simulate different densities.

Figure 4A:
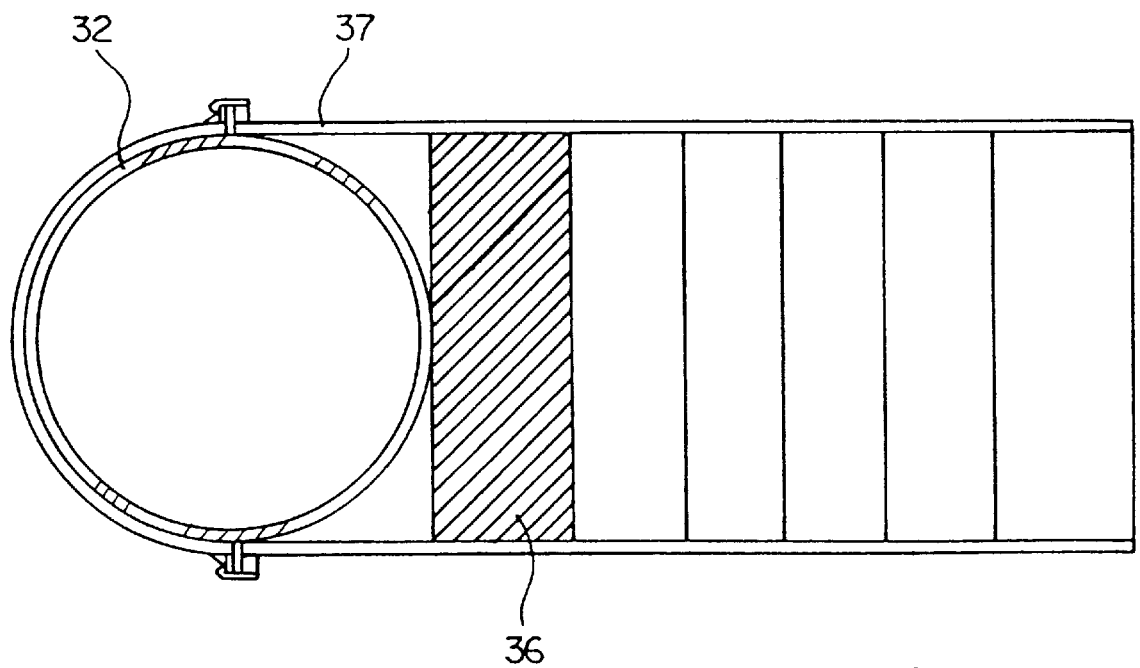
FIGS. 4A and 4B are cross-sectional top views of an interior view of a validation and calibration field test block showing an absorption element.

FIG. 4A shows a cross-sectional view within the block, taken along lines 4A—4A from FIG. 3. As shown in FIGS. 3 and 4A, the absorption element 36 in this embodiment increases in thickness with increasing depths i. A retainer cylinder 37 also is shown, surrounding the tube 32 and supporting the absorption element 36. As the insertion depth (i) of the source rod 24 increases, a large proportion of the detected photons will have higher energies. To reduce the number of high energy photons, more lead is needed to decrease the number of counts and thus to simulate the same densities as the lower source depth settings. To simulate higher densities, relatively more lead has to be used at greater depths in the block 30.

High density materials such as lead, tungsten, cadmium and other heavy elements are ideal as shielding materials for gamma rays, and thus are appropriate absorption elements. Such materials can be used individually or in combination with each other or other materials. The measurement of density by nuclear gauges is based on the detected counts from the test material. The magnitude of the detected counts depend on scattering and absorption proportions from the material. This proportion depends on the density of the material. Generally, an increase in material density causes higher absorption (photons are lost) and fewer detected scattering events. Therefore, with higher density materials, the gauge detected counts are lower than low density materials.

With this understanding of the photon absorption and scattering principles, one can simulate different density blocks by placing high density "filters" or absorption elements in the path of the radiation between the source and detectors. These "filters" cause absorption and allow sufficient photons to pass to the detectors to simulate a count similar to the counts collected on a known density reference. In a preferred embodiment, lead filters are used, having a density of approximately 11.34 g/cm3. Lead of differing thickness is used in the path between the source and the detectors, at each depth i, to simulate and achieve the same count on the gauge as what would be observed by the same gauge from a reference block of known density. Those skilled in the art can use the methods of this invention to place absorber materials of appropriate thickness in different locations in the radiation path between the source and the detectors to create an optimum field block for the density range of interest.

A total weight of a field block according to this invention can be approximately 12 kg (27 pounds). The block is light weight, convenient and can easily be transported manually by the gauge operator or on a truck for immediate use as a calibration validation indicator or, with an appropriate method, as a tool for generation of new calibration. The lead thickness necessary to simulate a density within the calibration range of the block is determined by using a gauge accurately calibrated on a set of known density reference blocks. This gauge is used on the field block and readings are taken with different thickness of lead until the desired density or count reading on the gauge is achieved.

In another embodiment, a field block with the density of magnesium (approximately 1.77 g/cm3) can be constructed. Using a magnesium block, an accurately calibrated gauge may obtain a certain count, e.g., 3000 counts. The same gauge is then placed on the field block and enough filter (e.g., lead) is placed in the radiation path between the source and the detectors to absorb the required number of photons to produce 3000 counts. Therefore, in this example, one can mark this field block to have the same density as magnesium when measured with the above gauge type. The same procedure can be followed for each source depth to determine a simulated block density based on an accurately calibrated gauge.

Figure 4B:
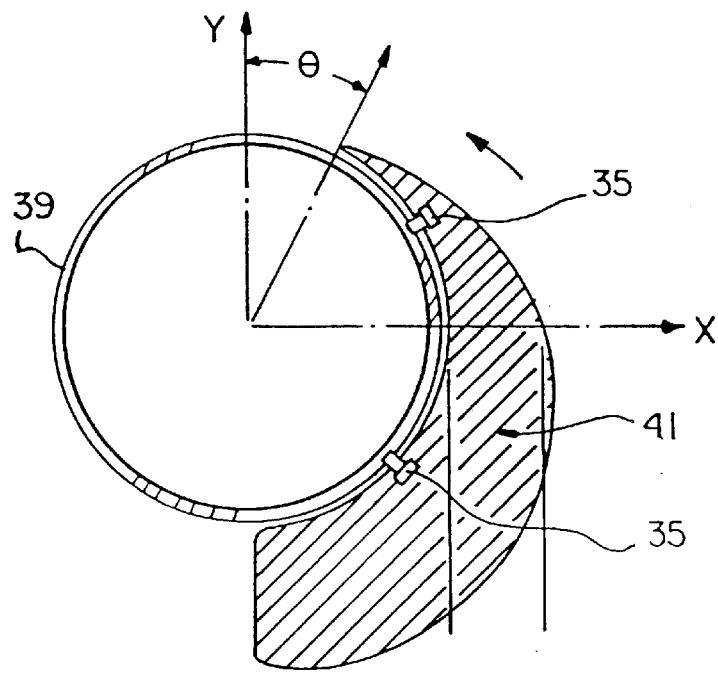

In alternative embodiments, the absorption elements can be used in different configuration, sizes and geometries at different locations in the radiation path between the source and the detector to produce the same density effect as the one described in the above embodiment. For example, FIG. 4B depicts an alternative geometrical configuration of a flared absorption element 41. Here, the element is rotatably mounted on a cylinder 39 forming an insertion tube. The mounting can occur through mechanical attachment means 35, or other suitable techniques well known in the art. The absorption element has a constant cross-section over the entire length of the insertion tube. During use, the cylinder 39 and absorption element 41 is rotated in the direction shown to obtain desired simulated densities. In one embodiment, the shape of the flared absorption element widens from 0 inches thickness at a theta ($\theta$) angle of about 25 degrees and depth of 2" to approximately 2.95" thickness at a theta ($\theta$) angle of about 180 degrees and depth of 12". Using lead as the absorber, this configuration will yield a simulated density reading. The flared absorption element is moved into an appropriate depth and/or position and angle in front of the source by either using a motorized means or manually by utilizing a handle or a lever capable of positioning the flared filter element into the radiation path between the source and the detectors.

Figure 5:
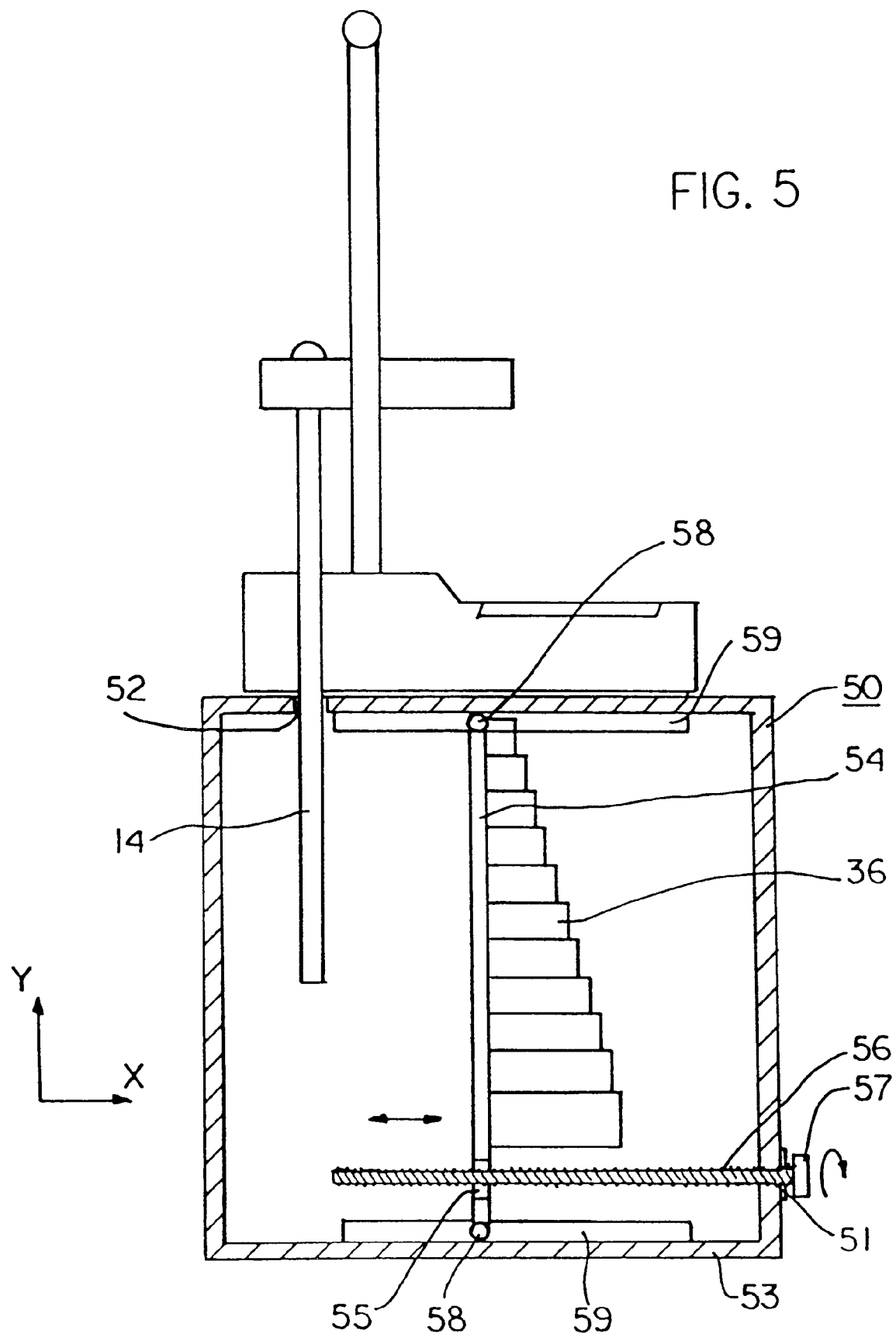
FIG. 5 is a cross-section of another embodiment according to this invention.

FIG. 5 shows another embodiment of this invention. In this field block 50, the insertion for the source rod consists of a 1" hole 52 to allow the penetration of the source rod 14 into a direct transmission position. The absorption material 36 is positioned on a support 54, which is translationally mounted to the enclosure 53. The mounting means can be any mechanical or electronic positioning apparatus that allows the support 54 to move in the X direction, as shown in FIG. 5. For example, a threaded rod 56 with accompanying dial 57 and metering plate 51 can be placed in a threaded opening 58 of the support structure, allowing the user to move the absorption element 36 to a desired set position within the enclosure 53. To facilitate ease of movement of the support 54, the support can be mounted on rollers 58, moving within guides 59. In this manner, the absorption element 36 can be placed at different distances from the hole 52 and source rod 14. Such variances can affect the simulated densities of the field block, since the radiation path geometry of the absorption element within the path between the source and the detectors is unchanged. Hence, multiple simulated densities are possible within the same field block 50. The field block can be calculated using an accurately calibrated gauge and positioning the element 36 at different locations with respect to the source rod 14. The user will then be supplied with calibration figures, such as the following:

| Simulated Density at 6 inches depth | Dial Position |
| --- | --- |
| 2200 kg/m$^3$ | 1 |
| 2100 kg/m$^3$ | 5 |
| 2000 kg/m$^3$ | 10 |
| 1900 kg/m$^3$ | 15 |
| 1800 kg/m$^3$ | 20 |

During calibration the figures in the first column above would be obtained using a nuclear gauge of known calibration. During use in the field, the user would turn the threaded rod 56 until the dial was pointed to the desired position on the metering plate 51. A suitable locking mechanism, which could be built into the rod 56/dial 57 and/or roller/guide assembly, can be included to ensure that the rod 56 and element 36 do not move during testing, after the desired location has been obtained. It is also possible to control the process by programmable controls from a computer or other electronic device.

FIGS. 6A and 6B show yet another embodiment. A cross-sectional view of a field block 60 is shown in FIG. 6A. An optional insertion hole 62 is placed in the top of the block, allowing for the insertion of a source rod (not shown). A support 64 is slidably mounted within the block, on guides 66. An absorption element 68 is positioned on the support 64, and can be placed at a designated height on the support 64, within the field block. In this manner, the absorption element 68 is placed in the radiation path between the source and detectors to simulate at least one density at each source rod setting.

The support 64 is removable from the field block through a door 70, shown at the rear of FIG. 6A. The door 70 is mounted by hinges 72, and secured through a closure 74.

FIG. 6A shows an alternative support 76, with absorption element 78. Element 78 is located at a different depth on the element 64, and can be of a different thickness to achieve the same or a different simulated density when placed in the field block. Elements are changed by opening the access door 70, sliding the existing support 64 out of the field block, and then placing the support 76 in the field block, along the guides 66.

Each support, 64 and 76 actually can serve as two different simulated densities by merely removing the element, inverting it, and replacing the element in the field block. Hence, the support 76 could function with an absorption element 78 located at a 4 inch height, as shown in FIG. 6B, or the same element positioned at a depth of 8 inches when inverted.

Each such support/absorption element assemblies as shown in FIGS. 6A and 6B will have sufficient and different thickness of absorber material as determined by an accurately calibrated gauge to simulate at least one density.

Figure 7A:
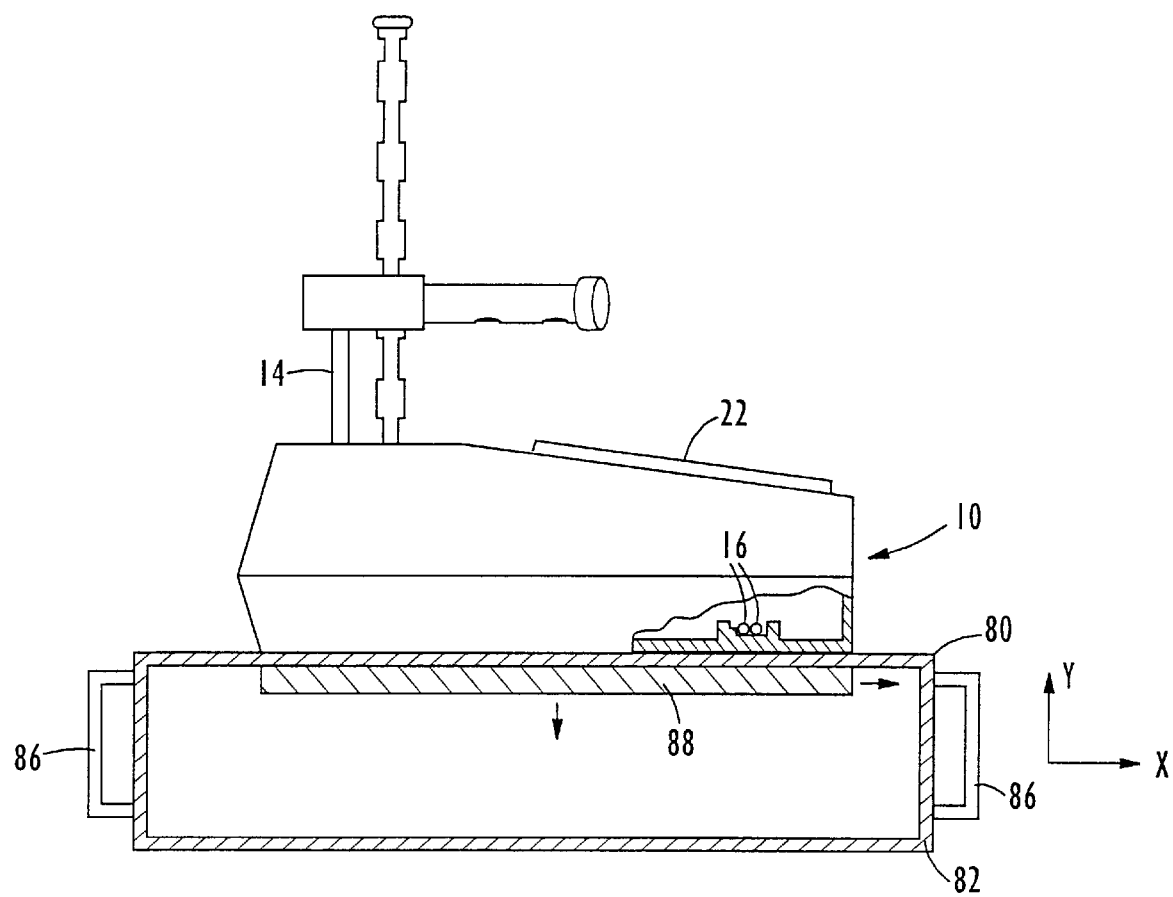
FIG. 7 is a cross section of a field block for use with backscatter tests according to this invention.

FIG. 7 shows another embodiment that does not use an insertion hole or tube. For nuclear density gauges that do not have direct transmission measurement capabilities, and are intended only for backscatter measurements, insertion holes are not needed. Hence, a field block 80 is provided, which has an optional surrounding shield 82 about an enclosure 84. Handles 86 are provided for ease of carrying. An absorption element 88 is positioned within the field block, yielding a simulated density. Of course, any of the other embodiments discussed above, minus the insertion hole, can also be adapted for a field block 80. For example, the absorption element 88 could be placed on a translational, threaded rod assembly to simulate multiple densities for a backscatter testing application. The element 88 can be moved in the X or Y directions as shown to simulate multiple densities.

Combined with appropriate software running the methodology as discussed below, and a personal computer (PC), or other electronic devices with computation capabilities such as hand held calculators, hand held portable scalars, or gauge internal processors, this product can display the calibration validation readings at different densities and generate new calibration constants at different gauge depths. For field use, an optional hand held programmable scalar or calculator can also be provided to allow the users access to the same information available on the PC program. Also, the process of validation and calibration described in this disclosure can be carried out in the field by programming the processor/computer in the nuclear gauge itself to allow even easier access to this method by the users.

Calibration Validation and Calibration Method

It is well known to those skilled in the art that gauge calibration can change with time due to several factors. Factors affecting gauge calibration include radioactive source decay, change in mechanical geometry such as deterioration of material, expansion of metals, bending of critical parts, movement of detectors, or other components, change in the detector efficiency over time (varies with amount of gauge usage), and electronic drift. Some of these changes are accounted for in the density calculation process of the gauge. The count ratio (gauge counts/std. count) corrects for source decay and minor electronic drifts over time. However, since the measurement geometry is significantly different in the gauge standard count position as compared to the actual test counts, other affects on the gauge calibration such as detector efficiency, mechanical geometry and major electronic component drifts can cause significant change in the gauge measurements. Thus, a new calibration is required due to the above factors and changes.

In a preferred embodiment, a block of predetermined density is used to calculate changes to the gauge counts due to decay factor (DF) and geometry factor (GF). GF is defined as the total of all effects not including the radioactive source decay. Once the factors affecting the gauge calibration are quantified, the gauge calibration validation can be tested and, if necessary, re-calibrations can be performed.

In this invention, a portable field block is used for calibration validation and new calibration. However, those skilled in the art will appreciate the fact that any block with a known density can be used with the teachings of this invention for the determination of gauge calibration validation and new calibration at all depths and modes of operation.

Validate The Gauge Calibration

Once an appropriate density is assigned to the field block as discussed above, it can be used for validation of gauge calibration. Validation is performed as follows:

Place the nuclear gauge on the field block (or place the field block in the measurement zone of the gauge).

Take gauge readings at all operating positions or modes of the gauge.

Compare the gauge density measurements to the assigned density values of the field block for all the positions and modes of measurement.

If the absolute value of the % error between the gauge density readings and the assigned field density is above a predetermined value, for example 1%, then the gauge calibration is outside the required limit and a new calibration needs to be performed on the gauge.

Where,

% error=[(Field block density-Gauge measured density)/(Field block density)]*100

Note: The error limit acceptable to the user depends upon the user's testing procedures and requirements.

Validate The Gauge Calibration For Differing Densities

A further embodiment of this invention relates to validating the gauge operation at different densities within the density measurement range of interest. For example, in the construction industry, an asphalt density might be between 2.3 g/cm$^3$ to 2.4 g/cm$^3$. If the field block density is below this range, for example 1.92 g/cm$^3$, the user might want to know if the gauge calibration is accurate not only at 1.92 g/cm$^3$ but at several densities between 2.3 g/cm$^3$ and 2.4 g/cm$^3$. In this case, the gauge counts on the field block, the field block density and the gauge calibration can be used to accomplish this task, as set forth below. The validation and calibration method described in this disclosure requires the gauge to have been calibrated at the factory at least once. The factory calibration parameters are used throughout this method for calibration validation and for generating new calibrations.

Figure 8A:
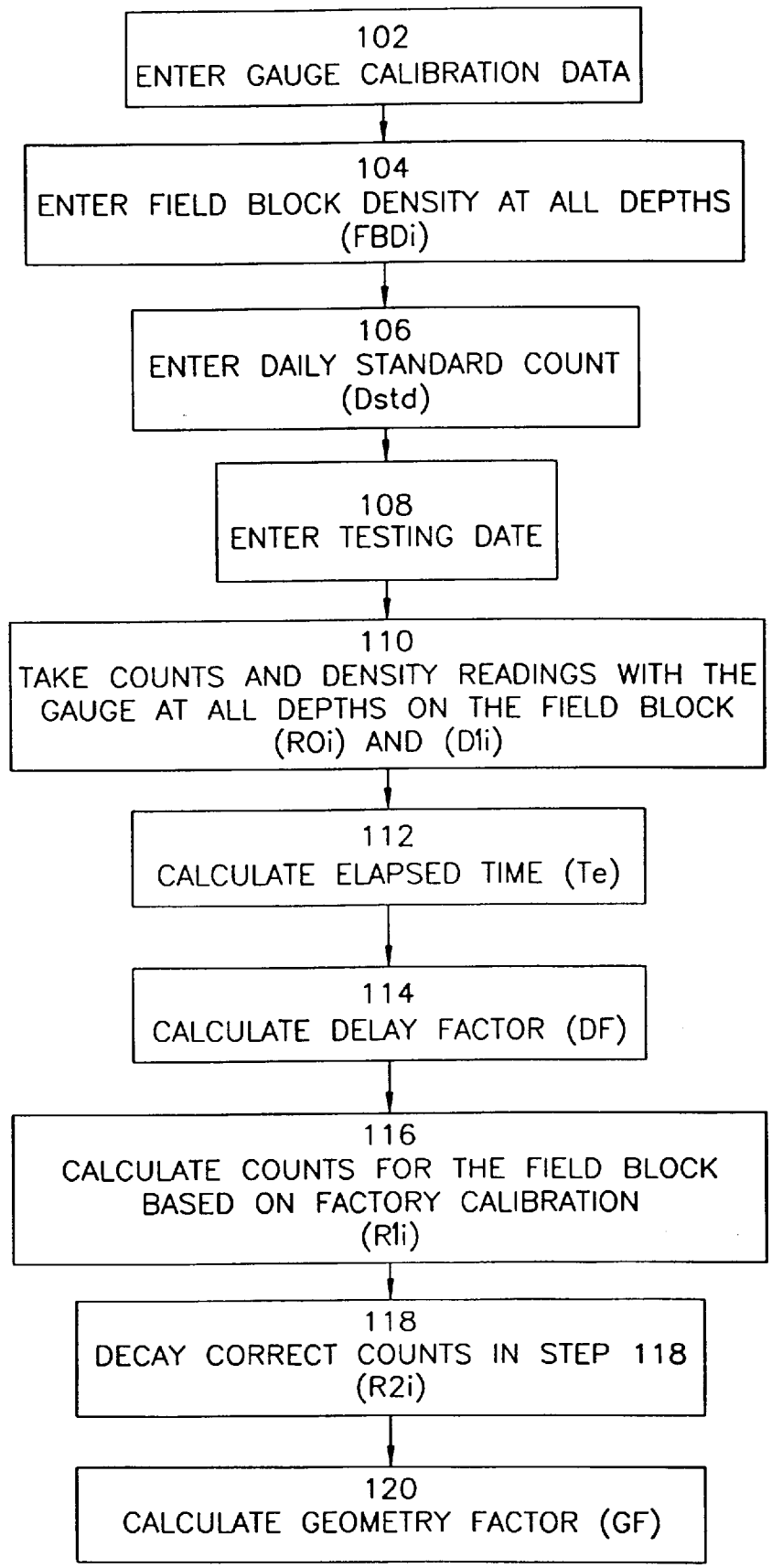
FIGS. 8A, 8B, and 8C depict flow charts indicating methods according to this invention.
Figure 8B:
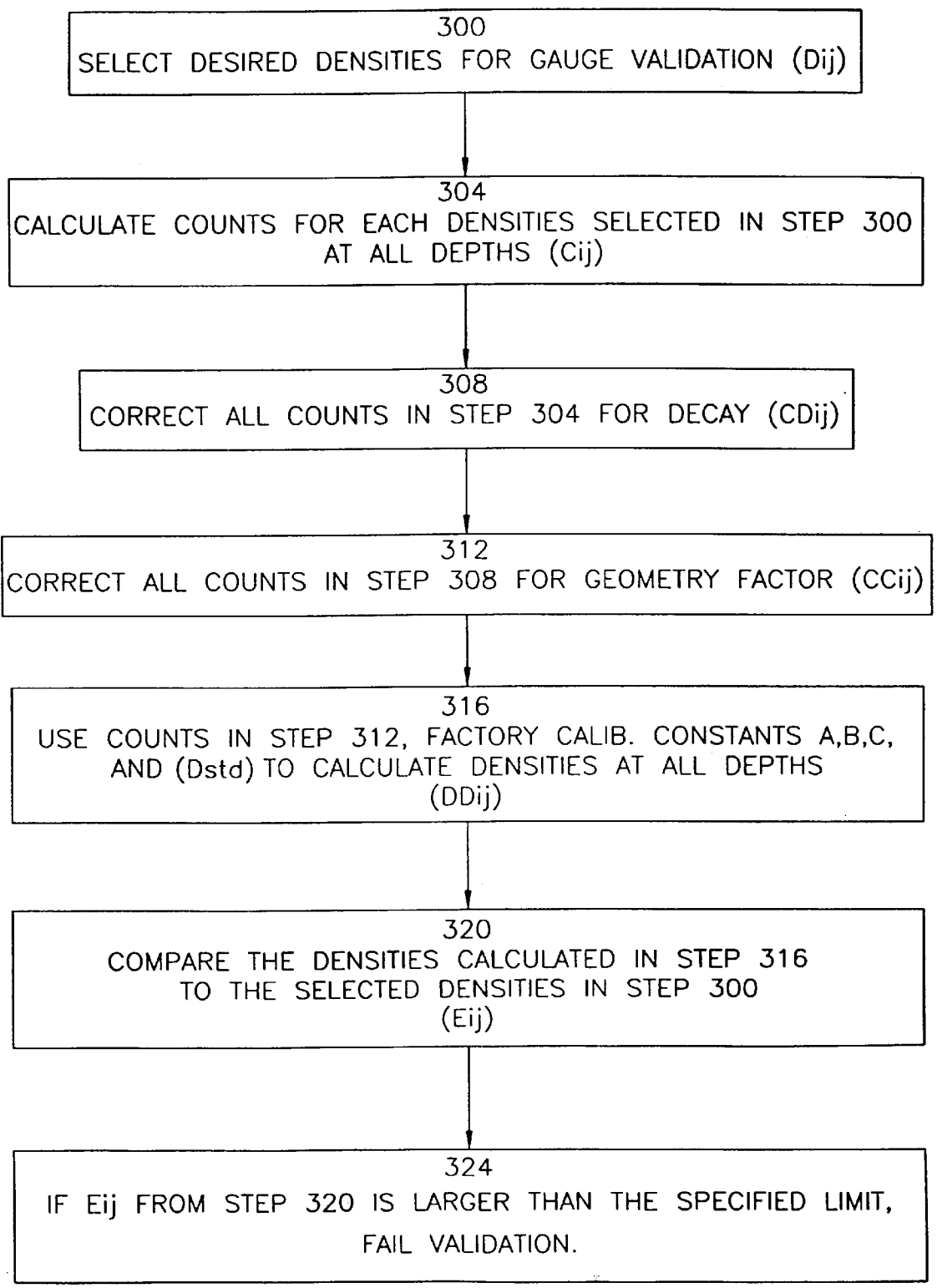
Figure 8C:
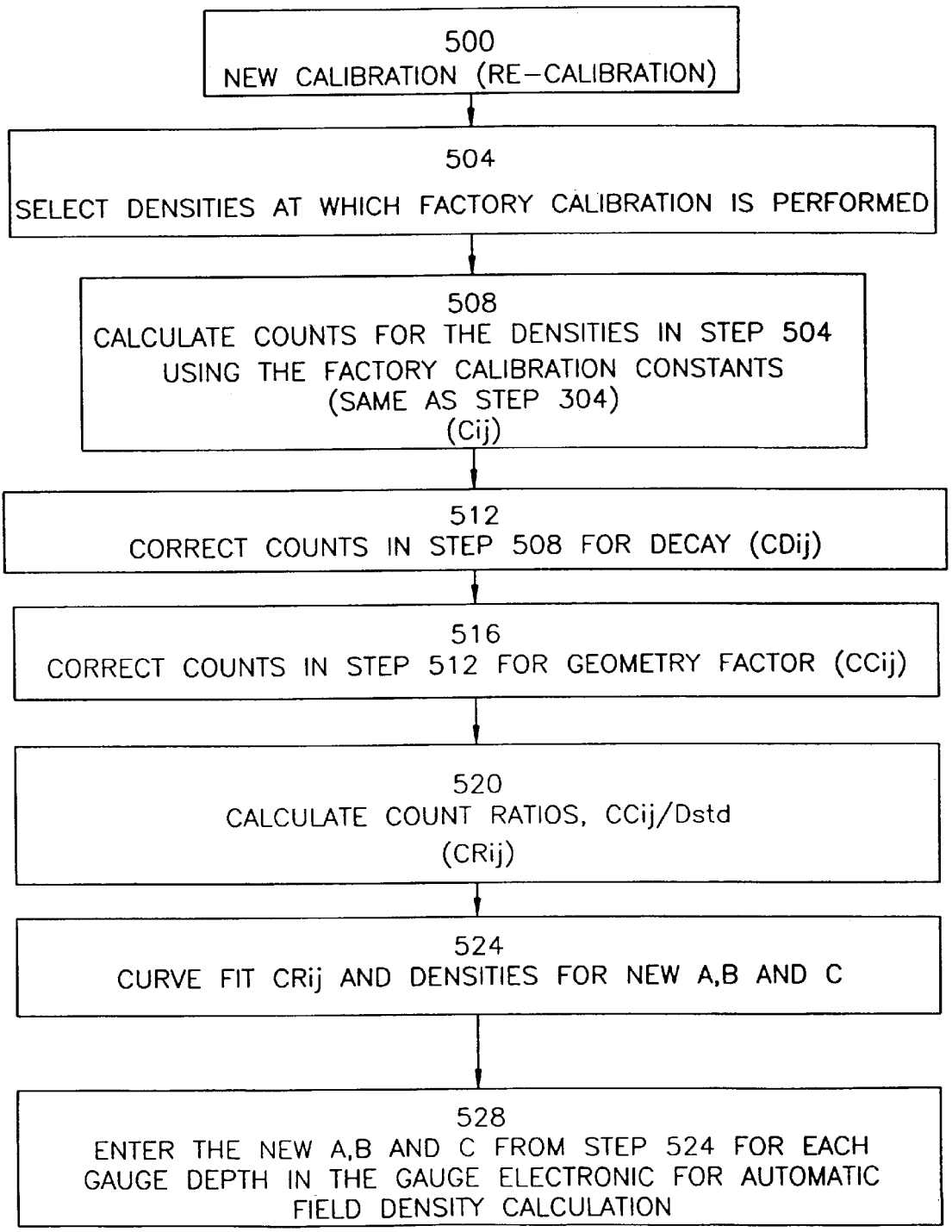

In a preferred embodiment, software is provided to allow the input, recordation and calculation of desired parameters. FIGS. 8A through 8C illustrate the methodology employed in a preferred embodiment.

As shown in FIG. 8A, in Step 102, specific gauge factory calibration data is entered into the computer program. Such gauge data can include the gauge model, gauge serial number, gauge calibration date, gauge calibration constants (A, B and C) for depths of 0 through 12 inches, etc. Next, the simulated field block density (FBD$_i$) for i=0 to 12" depth is entered in Step 104. In 106, a gauge reading of the standard count (Dstd) is taken on the reference block provided with the gauge. The date that the readings are being taken is entered at Step 108.

In Step 110, take counts (R0i) and densities D1i measured by the gauge, for i=0 to 12" depth on the field block.

At this point, the operator can compare the density readings displayed on the gauge (Step 110) versus the density provided for each depth for the field block (entered in Step 104) and determine if the readings are within the acceptable range of errors, as described in the last section (e.g., within +/−1%). Alternatively, software can calculate the % error in the readings, as set forth below.

Step 112: Calculate the elapsed time (Te) in number of days from the gauge's calibration date and the day of measurements.

$$Te=(\text{Calibration date-Test date})$$

Step 114: calculate the decay factor, DF $$DF=\exp(-\lambda * Te)$$

where
- λ=decay constant (e.g., 0.693/T$_{1/2}$), and T$_{1/2}$ is the half life of the source (e.g., 30 years for Cesium-137), defined as the period during which the activity of the source falls by a factor of two
- Te=elapsed time in days from the calibration date Step 116: Using the field block density provided (FBD$_i$) for i=0 to 12" depth in Step 104, the gauge calibration constants A$_i$, B$_i$ and C$_i$ in Step 102 and the daily reference standard count (Dstd) from Step 106, calculate what the field block counts would have been, if they were taken on the day of gauge calibration, in accordance with the following formula:

$$R1i=Std*A_i*\exp(-B_i*FBD_i)-C_i \text{ for } i=0 \text{ to } 12"$$

Step 118: Based on the elapsed time calculated in Step 112, correct the R1i counts for decay using the decay factor in 114 with the following formula:

$$R2i=R1i*DF$$

Thus, R2i is the theoretical count for the field block as if the change in gauge counts from the day of calibration was only due to decay of the radioactive source. Other changes in counts can also occur with the passage of time due to changes in detector efficiency, change in gauge mechanical geometry and change in the electronic components of the gauge.

Step 120: To Calculate the total affect of other change factors (geometry factor GF) on the gauge, R0i and R1i counts, for i=0 to 12" depth, should be compared $$GF=(R0i-R2i)/R0i$$

Validation of Gauge at Multiple Desired Densities

FIG. 8B illustrates the method by which a field gauge is validated at multiple desired densities.

Step 300: Select desired densities Dij at which calibration validation is desired. The densities Dij are selected at each gauge depth i=1 to 12" and density increments of j=1 to ∞ within the range of the gauge calibration.

Step 304: Based on the gauge calibration parameters and selected densities D$_{ij}$ calculate counts C$_{ij}$. Where, i=0 to 12" and j=1 to ∞ number of density increments, according to the following formula:

$$C_{ij}=Std*A_i*\exp(-B_i*D_{ij})-C$$

where, std. is the factory standard count.

Step 308: Correct counts Cij in Step 304 for decay $$CDij=Cij*DF$$

Step 312: Correct the CD$_{ij}$ values in Step 308 by Geometry Factor (GF) as follows:

$$CCij=CDij*(1+GF)$$

This will insure that these counts are corrected for all the changes (decay, electronic and mechanical) in the gauge, since the day of calibration.

Step 316: Use the corrected counts from Step 312 and the calibration constants Ai, Bi, Ci and Dstd (from Step 106) to calculate density values DDij as follows:

$$DDij=(1/Bi)*\ln(Ai/Crij+Ci)$$

where, Crij is the count ratio (CCij/Dstd).

Step 320: Calculate % error (Eij) by $$Eij=100*((Dij-DDij)/Dij)$$

Step 324: If the absolute value of Eij is 1% or less, the user likely can continue using the gauge with confidence that the unit has an adequate calibration. This percentage can be determined by the user depending on the level of accuracy required.

Those skilled in the art are not limited to the use of this field block merely to validate a previous calibration. A new calibration may also be obtained, as outlined below.

Calibration Process

To establish a new calibration, the gauge must have had at least one previous calibration. Gauges are always calibrated by the manufacturer before shipment to the customer. Gauges are calibrated by using sufficient number of counts and density pairs to determine the factory calibration equation constant parameters. In this case, equation (1) has constant parameters A, B and C for each depth. Therefore, three counts and density pairs are required to determine the parameters A, B and C by an appropriate fitting routine.

This invention provides a method by which the gauge can be calibrated after validation has failed. However, the calibration process in this invention can be performed without initially performing the validation process. The calibration process is done by using the counts and density of the field block to quantify changes in the gauge counts since the day of factory calibration (e.g., DF and GF of Steps 114 and 120, respectively). Based on these factors, sufficient corrected counts for given densities are calculated using the original factory calibration of the gauge. These counts and the corresponding densities are then used to calculate the factory calibration equation constant parameters.

FIG. 8C illustrates the method of calibration according to an embodiment of this invention. Those skilled in the art can use the teachings of this invention with counts obtained with one block of known material and gauge's factory calibration to generate new calibrations for different calibration ranges within the original calibration range of the gauge. The steps of FIG. 8C are discussed below.

Step 500: If new calibration is desired, select at least three count and density pairs.

Step 504: To comply with the method originally used by the gauge manufacturer for the gauge, select the densities at which the gauge was originally calibrated.

Step 508: Calculate the corresponding counts for the densities selected in Step 504. These counts are calculated in the same manner as Step 304 (i.e. Cij).

Step 512: Correct the counts in Step 508 by the decay factor DF of Step 114.

Step 516: Correct the counts in Step 512 by the geometry factor, GF, of Step 120.

Step 520: Calculate Count ratios by dividing the counts in Step 512 by the daily std count Dstd. of Step 106.

Step 524: Use an appropriate computer fitting routine to determine the parameters A, B and C.

Step 528: Enter the constants A, B and C into the gauge electronics for automatic calculation of density from field measured counts.

FIGS. 9A, 9B, 9C and 9D illustrate some of the methods used in this invention to accomplish nuclear gauge validation and calibration with either the field block and/or other blocks of known density.

Figure 9A:
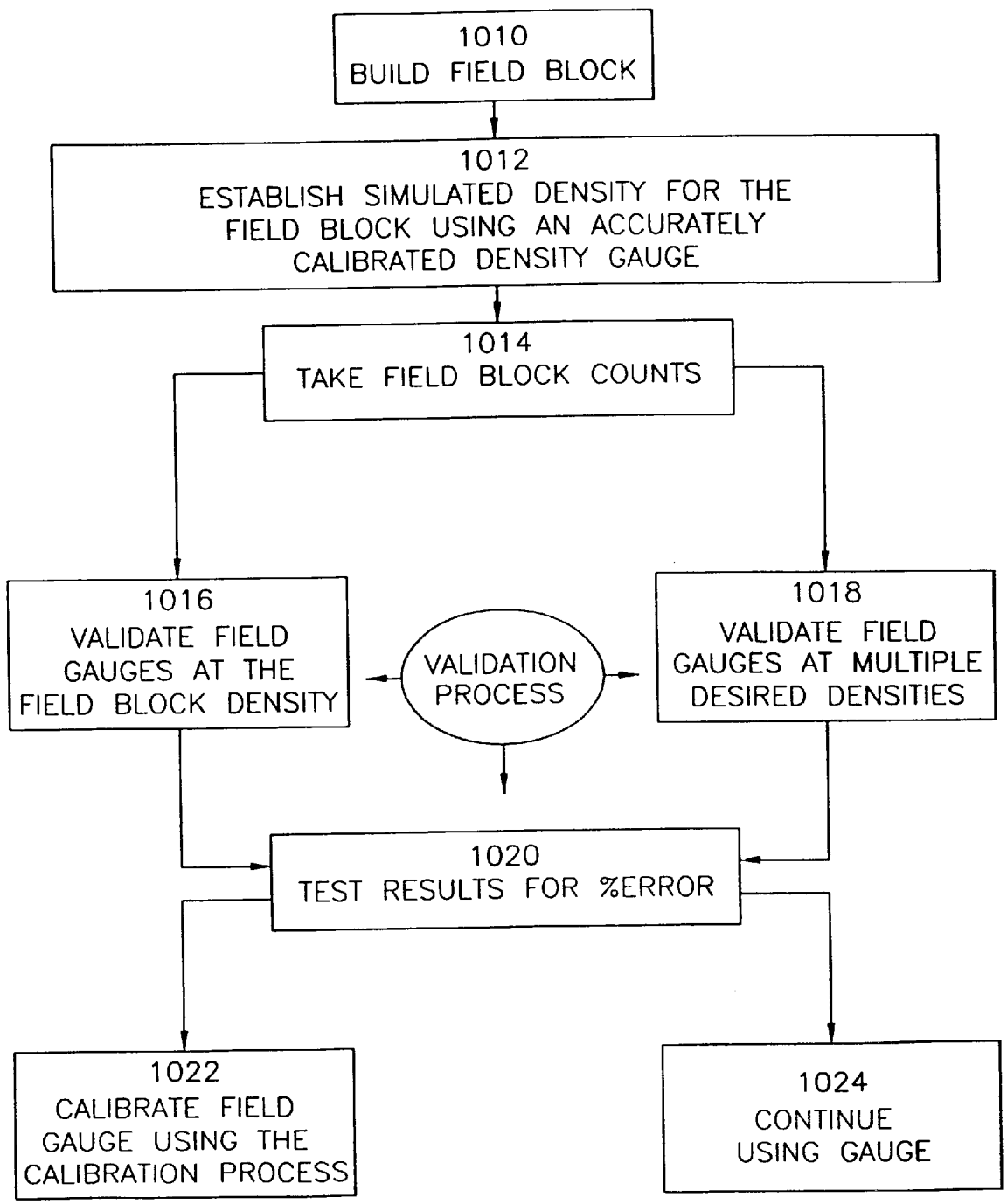
FIGS. 9A, 9B 9C and 9D depict additional flow charts indicating methods according to this invention.

In FIG. 9A, a field block is first constructed 1010 as described herein. Next, the simulated densities are established 1012 for the block using an accurately calibrated nuclear gauge. With assignment of the density, the field block can be used for the validation and/or calibration of the gauges used in the field as described in this invention. Next field block counts are taken 1014 using the nuclear density gauge of interest. The user has the option of either validating 1016 the gauge at the field block density, or validating 1018 the gauge at multiple desired densities (see FIG. 8B and accompanying discussion). From either method, the test result error percentages are then calculated 1020. If the error percentages are within acceptable tolerances, the user can continue to use the gauge 1024. If not, the gauge should be re-calibrated 1022 as described herein.

Figure 9B:
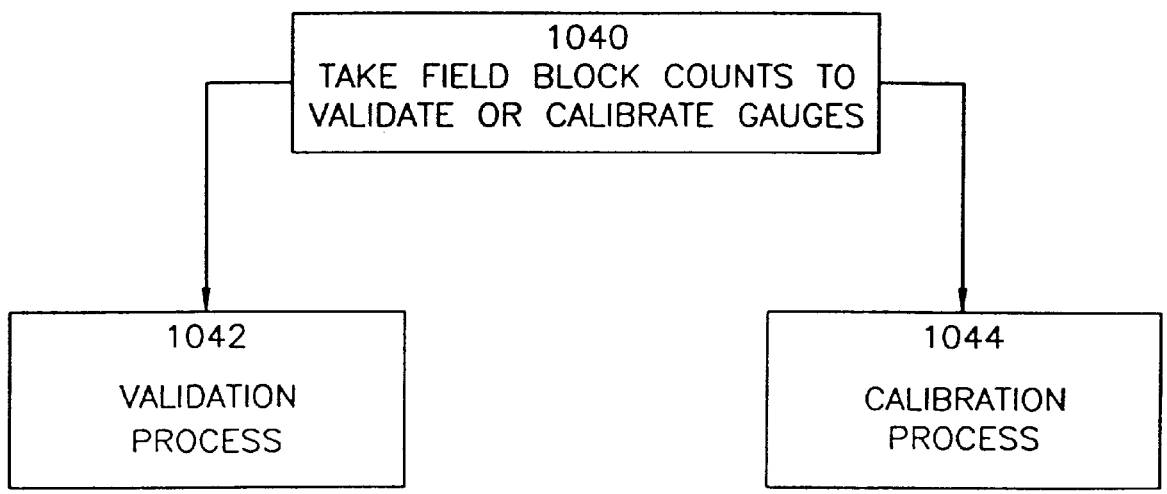

FIG. 9B illustrates that the validation 1042 and/or the calibration 1044 process can be carried out in the field 1040. It is not necessary to validate the gauge prior to calibration. Each process can be performed independent of the other.

Figure 9C:
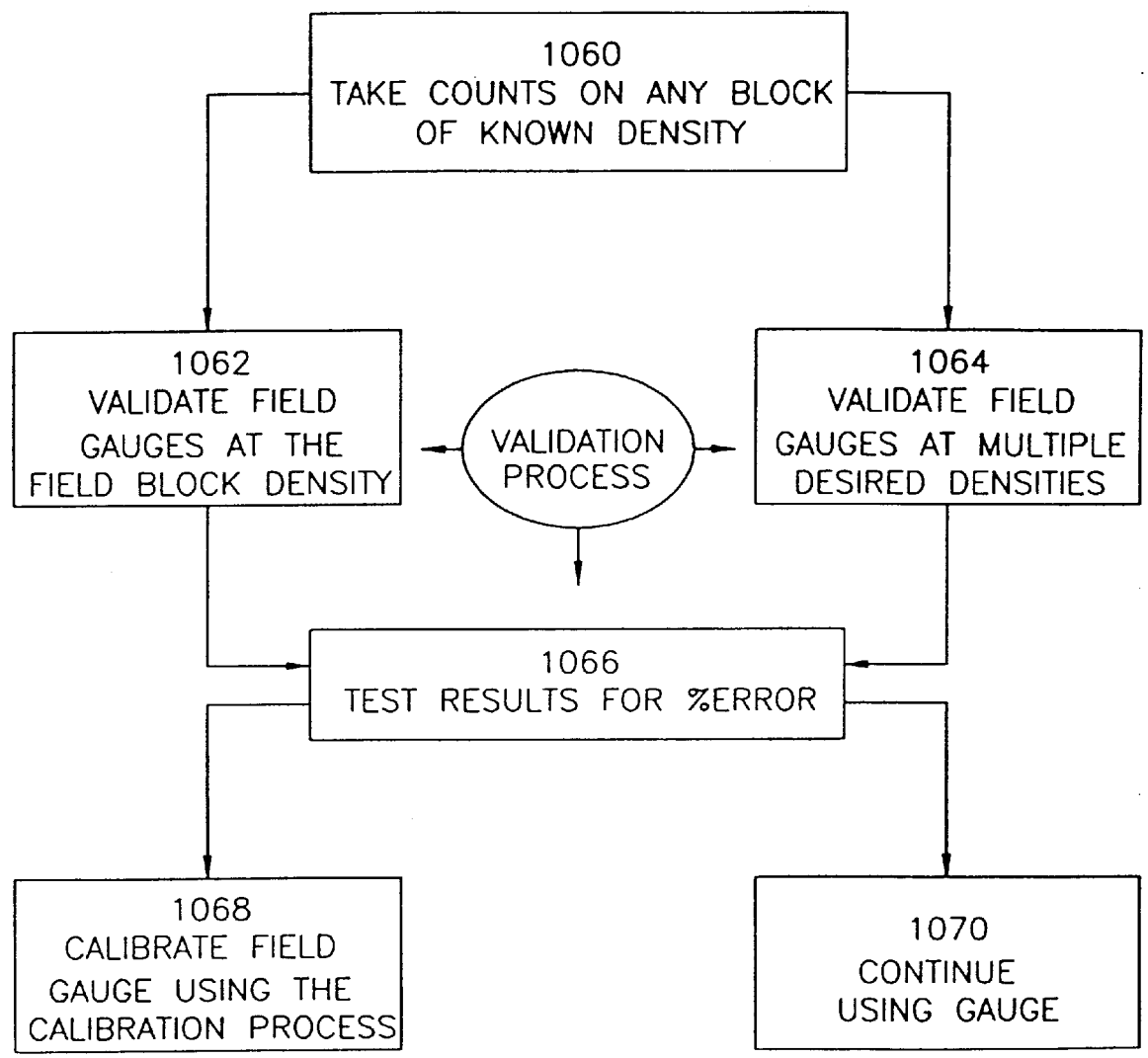

FIG. 9C illustrates steps that are analogous to those outlined in FIG. 9A. The difference is that a field block with simulated densities is not used. Instead, counts are taken 1060 on any block of known density. This could be a reference block supplied by the gauge manufacturer, or maintained by the gauge user. Once the counts are taken, the gauge can be validated at the reference block density 1062, or at multiple desired densities 1064 using the methods described above. Error results are evaluated 1066, leading to continued use of the block 1070, or re-calibration 1068. This example illustrates that, although the field block provides a convenient method of measurement, other blocks of known density can be employed for carrying out gauge calibration and/or validation.

Figure 9D:
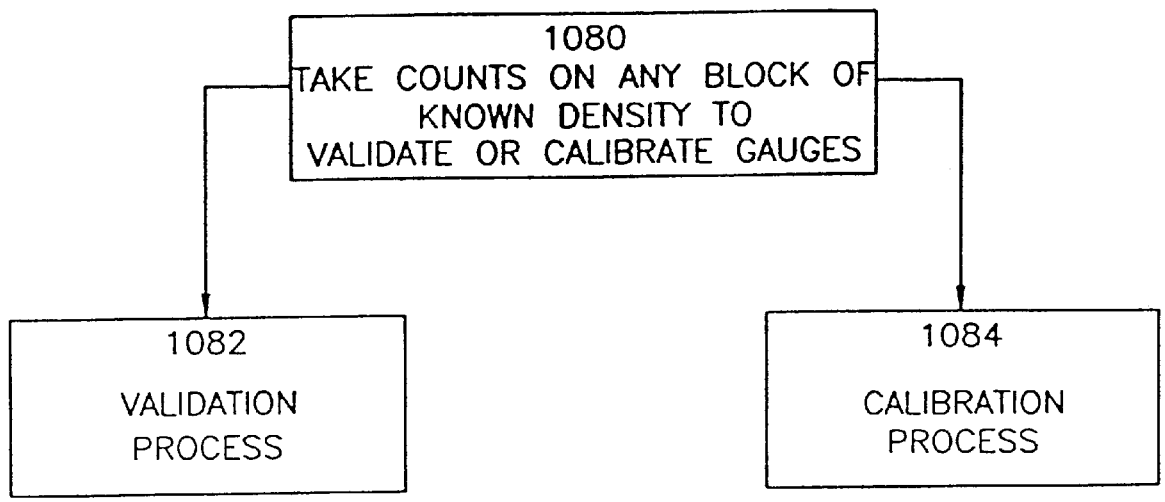

FIG. 9D illustrates steps analogous to those outlined in FIG. 9B. The only difference is the block used in collecting the gauge counts for the validation and/or the calibration process. Any block of known density can be used to accumulate the counts necessary to carry out the validation and/or the calibration process described in this disclosure. Counts are taken on the block of known density 1080. Then, the user can elect to either validate 1082 and/or calibrate 1084 as discussed above.

EXAMPLE

The following example further illustrates an embodiment of this invention.

| Enter Gauge Factory Calibration Information (Step 102) | |
|---|---|
| Gauge Model | 3430A |
| Gauge Serial Number | 19509 |
| Mag Density (Kg/m3) | 1760 |
| Mag/Alum Density (Kg/m3) | 2137 |
| Alum Density (Kg/m3) | 2598 |
| Calibration Standard Count | 2857 |
| Gauge Calibration Date | 2/6/91 |

| Enter Gauge Factory Calibration Constants | | | |
|---|---|---|---|
| Depth | A | B*1000 | C |
| 0 | 4.303 | 1.41163 | −0.09956 |
| 2 | 13.404 | 1.28369 | −0.17015 |
| 4 | 17.545 | 1.40344 | −0.12253 |
| 6 | 19.02 | 1.55169 | −0.06347 |
| 8 | 22.338 | 1.85218 | −0.05216 |

| Enter Field Block Density (Step 104) | |
|---|---|
| Depth | FBDi |
| 0 | 1922 |
| 2 | 1922 |
| 4 | 1922 |
| 6 | 1922 |
| 8 | 1922 |
| Daily Standard Count (Step 106) | 2808 |
| Valid./Calib. Date (Step 108) | 7/27/94 |

| Counts Collected on the Field Block (Step 110) | | |
|---|---|---|
| Depth | R0i | D1i |
| 0 | 933 | 2067 |
| 2 | 3357 | 2002 |
| 4 | 3373 | 1987 |
| 6 | 2632 | 1985 |
| 8 | 1754 | 1978 |
| Elapsed Time, Te (Step 112) | | 1251 |
| Decay Factor, DF (Step 114) | | 0.922864 |

| Correct For Source Decay DF and Calculate Geometry Factors DF Step 116 Step 118 Step 120 | | | |
|---|---|---|---|
| Depth | R1i | R2i | GF |
| 0 | 1100 | 1015 | −0.0879 |
| 2 | 3734 | 3446 | −0.02657 |
| 4 | 3728 | 3440 | −0.01987 |
| 6 | 2935 | 2709 | −0.02909 |
| 8 | 1964 | 1813 | −0.03345 |

| Select Densities to Check Validation (Kg/m3), Dij (Step 300) | | | | | | | |
|---|---|---|---|---|---|---|---|
| 1700 | 1800 | 1900 | 2000 | 2100 | 2200 | 2300 | 2400 |

| Calculate Counts at Desired Densities, (Steps 304, 308 and 312) | | | | | | | | |
|---|---|---|---|---|---|---|---|---|
| Depth | 1700 | 1800 | 1900 | 2000 | 2100 | 2200 | 2300 | 2400 |
| 0 | 1158 | 1037 | 931 | 840 | 760 | 691 | 631 | 579 |
| 2 | 4243 | 3783 | 3379 | 3024 | 2711 | 2436 | 2195 | 1982 |
| 4 | 4411 | 3875 | 3408 | 3003 | 2650 | 2344 | 2078 | 1846 |
| 6 | 3582 | 3090 | 2669 | 2308 | 1999 | 1735 | 1509 | 1315 |
| 8 | 2531 | 2125 | 1788 | 1508 | 1275 | 1082 | 921 | 787 |

| Calculate Gauge Densities (kg/m3), DDij (Step 316) | | | | | | | | |
|---|---|---|---|---|---|---|---|---|
| Depth | 1700 | 1800 | 1900 | 2000 | 2100 | 2200 | 2300 | 2400 |
| 0 | 1857 | 1962 | 2069 | 2176 | 2284 | 2394 | 2506 | 2620 |
| 2 | 1793 | 1895 | 1996 | 2098 | 2200 | 2303 | 2405 | 2508 |
| 4 | 1777 | 1878 | 1979 | 2080 | 2182 | 2283 | 2385 | 2487 |
| 6 | 1774 | 1875 | 1976 | 2076 | 2177 | 2278 | 2380 | 2481 |
| 8 | 1765 | 1866 | 1967 | 2068 | 2169 | 2271 | 2373 | 2475 |

-continued

Calculate % Error in Desired Densities and Calculated Gauge Densities,

Eij (Step 320)

| Depth | 1700 | 1800 | 1900 | 2000 | 2100 | 2200 | 2300 | 2400 |
|---|---|---|---|---|---|---|---|---|
| 0 | −9.23 | −9.02 | −8.87 | −8.80 | −8.78 | −8.84 | −8.96 | −9.15 |
| 2 | −5.50 | −5.27 | −5.08 | −4.91 | −4.77 | −4.66 | −4.58 | −4.51 |
| 4 | −4.54 | −4.34 | −4.16 | −4.01 | −3.88 | −3.78 | −3.69 | −3.62 |
| 6 | −4.37 | −4.16 | −3.98 | −3.82 | −3.68 | −3.56 | −3.46 | −3.38 |
| 8 | −3.84 | −3.67 | −3.52 | −3.40 | −3.30 | −3.22 | −3.16 | −3.12 |

Caution : Errors Above 1%, Gauge Failed Validation, (Step 324)

Generate New Calibration Constants

Select Densities, (Step 504)

| | |
|---|---|
| Mag Density (Kg/m3) | 1760 |
| Mag/Alum Density (Kg/m3) | 2137 |
| Alum Density (Kg/m3) | 2598 |

Calculate Counts For Mag, Mag/Alum and Alum Blocks, (Steps 508, 512, 516)

| Depth | Alum | M/A | Alum |
|---|---|---|---|
| 0 | 1310 | 887 | 599 |
| 2 | 4487 | 2951 | 1850 |
| 4 | 4592 | 2848 | 1658 |
| 6 | 3724 | 2154 | 1146 |
| 8 | 2601 | 1368 | 668 |

Calculate Count Ratios, CRij (Step 520)

| CR1 | CR2 | CR3 |
|---|---|---|
| 0.392694 | 0.265893 | 0.17956 |
| 1.435499 | 0.944096 | 0.591859 |
| 1.479199 | 0.917412 | 0.534084 |
| 1.188311 | 0.687331 | 0.365683 |
| 0.82624 | 0.436522 | 0.213156 |

Curvefit To Obtain the Gauge Constants, (Step 524)

| Depth | A | B*1000 | C |
|---|---|---|---|
| 0 | 3.668254 | 1.408753 | −0.08516 |
| 2 | 12.25163 | 1.283691 | −0.15552 |
| 4 | 16.147 | 1.40344 | −0.11277 |
| 6 | 17.33993 | 1.551693 | −0.05787 |
| 8 | 20.36426 | 1.852181 | −0.04755 |

The calculations performed in the above example can be performed in any standard spreadsheet or other computer program. The software can be written to be operable in a WINDOWS environment, with appropriate user interfaces and prompts. The calculations referenced herein, for example, can be performed using MICROSOFT EXCEL V. 7.xx. The curve fitting method referenced in Steps 524, 1022, 1044, 1068, and 1084 of FIGS. 8C, 9A, 9B, 9C and 9D can be performed using the SOLVER function, within the TOOLS menu of EXCEL.

The above description of the preferred embodiments thus detail many ways in which the present invention can provide its intended purposes. While several preferred embodiments are described in detail hereinabove, it is apparent that various changes might be made without departing from the scope of the invention, which is set forth in the accompanying claims.

I claim:

1. A field block for use with a nuclear density gauge comprising an absorption element, wherein said absorption element is capable of simulating at least one known density when subjected to analysis using the nuclear density gauge, said field block further comprising an enclosure, said absorption element being positioned inside said enclosure, and wherein said enclosure comprises a material having a density sufficient to substantially block radiation generated by the nuclear density gauge from exiting said enclosure.

2. A field block for use with a nuclear density gauge comprising an absorption element, wherein said absorbtion element is capable of simulating at least one known density when subjected to analysis using the nuclear density gauge, wherein the nuclear density gauge comprises a source rod and a detector and the field block further comprises an insertion tube positioned within said enclosure and capable of receiving the source rod for the purpose of conducting direct transmission nuclear density readings, and wherein said absorption element is positioned on said insertion tube.

3. A field block for use with a nuclear density gauge comprising an absorption element, wherein said absorption element is capable of simulating at least one known density when subjected to analysis using the nuclear density gauge, wherein said absorption element is capable of simulating a plurality of different densities when subjected to testing by the nuclear density gauge.

4. A field block for use with a nuclear density gauge comprising an absorption element, wherein said absorption element is capable of simulating at least one known density when subjected to analysis using the nuclear density gauge, said field block further comprising an enclosure, said absorption element being positioned inside said enclosure, and wherein said absorption element has a plurality of positions within said enclosure, and the nuclear density gauge will perceive a corresponding plurality of simulated density readings, when said absorption element is placed in said plurality of positions.

5. A field block for use with a nuclear density gauge comprising an absorption element, wherein said absorption element is capable of simulating at least one known density when subjected to analysis using the nuclear density gauge, wherein the nuclear density gauge comprises a source rod and a detector and the field block further comprises an insertion tube positioned within said enclosure and capable of receiving the source rod for the purpose of conducting direct transmission nuclear density readings, wherein said insertion tube has a depth allowing the source rod of the nuclear density gauge to take a plurality of readings at increments along the depth, and wherein said absorption element substantially simulates at least one desired density at each of the plurality of depth positions.

6. A field block for use with a nuclear density gauge comprising an absorption element, wherein said absorption element is capable of simulating at least one known density when subjected to analysis using the nuclear density gauge, and wherein said absorption element is lead.

7. A field block for use with a nuclear density gauge comprising an absorption element, wherein said absorption element is capable of simulating at least one known density when subjected to analysis using the nuclear density gauge, wherein the nuclear density gauge comprises a source rod and a detector and the field block further comprises an insertion tube positioned within said enclosure and capable of receiving the source rod for the purpose of conducting direct transmission nuclear density readings, wherein said absorption element increases in thickness as the depth of the insertion tube increases.

8. A field block for use with a nuclear density gauge comprising an absorption element, wherein said absorption element is capable of simulating at least one known density when subjected to analysis using the nuclear density gauge, wherein the nuclear density gauge comprises a source rod and a detector and the field block further comprises an insertion tube positioned within said enclosure and capable of receiving the source rod for the purpose of conducting direct transmission nuclear density readings, and wherein said absorption element increases in thickness radially from said insertion tube.

9. The field block of claim 8 where the absorption element is rotatably mounted within the enclosure.

10. The field block of claim 8 where the absorption element has the same shape along the length of the insertion tube.

11. A method of constructing a field block for use with a nuclear density gauge comprising:
   a. providing an absorption element;
   b. taking a reading using the absorption element with a calibrated nuclear density gauge to determine if the field block simulates a desired density;
   c. if necessary, altering the composition or configuration of the absorption element and retaking the reading with the nuclear test gauge until the gauge gives a density reading substantially the same as the desired density.

12. The method of claim 11, further comprising providing an enclosure for the absorption element, wherein said enclosure is lined with a photon absorbing material.

13. A method of validating the calibration of a nuclear density gauge, which is capable of determining densities at incremental depths, comprising:
   a. providing a block with known densities per incremental depth;
   b. providing a nuclear density gauge;
   c. taking counts and density readings of the block using the nuclear gauge;
   d. validating the calibration of the gauge by comparing the nuclear density gauge readings with the known densities per incremental depth.

14. The method of claim 13 where the block with a known density is a field block comprising an absorption element which simulates a known density.

15. A method of validating a nuclear density gauge at multiple desired densities, where the gauge has an existing calibration and related constants, comprising:
   a. selecting a plurality of desired densities;
   b. providing a nuclear density gauge with the ability to take readings incrementally at a plurality of source rod depths;
   c. providing a block with a known density;
   d. obtaining counts on the block with a known density;
   e. calculating counts at each selected desired density at each incremental depth, using the gauge's existing calibration constants;
   f. correcting all counts for decay;
   g. correcting all counts for electronic and mechanical changes in the gauge;
   h. calculate densities for all corrected counts at all incremental depths;
   i. validate gauge by comparing calculated densities with selected desired densities.

16. The method of claim 15, wherein said block with a known density is a field instrument comprising an absorption element which simulates a known density.

17. The method of claim 15 wherein said block with a known density is a reference block of known density and composition.

18. A method of re-calibrating a nuclear density gauge comprising
   a. selecting a plurality of desired densities;
   b. providing a nuclear density gauge with the ability to take readings incrementally at a plurality of source rod depths;
   c. providing a block with a known density;
   d. obtaining counts on the block with a known density;
   e. calculating counts at each selected desired density at each incremental depth, using the gauge's existing calibration constants;
   f. correcting all counts for decay;
   g. correcting all counts for electronic and mechanical changes in the gauge;
   h. calculate count ratio by dividing calculated counts by a daily standard count taken on reference block provided with gauge;
   i. re-calibrating the gauge by determining constants A, B and C at each depth according to following equation at each depth using a curve-fitting method $$CR = A\, e^{(-BD)} - C$$

where CR is a ratio of the count on the block of known density and the daily standard count; A, B and C are gauge parameters for each depth; and D is the material density.

19. The method of claim 18 where the block with a known density is a field block comprising an absorption element which simulates the known density.

20. The method of claim 18, wherein said block with a known density is a reference block of known density and composition.

21. A method of validating a nuclear density gauge at multiple desired densities, where the gauge has an existing calibration and related constants, comprising:
   a. selecting a plurality of desired densities;
   b. providing a nuclear density gauge;
   c. providing a block with a known density;
   d. obtaining counts on the block with a known density;
   e. calculating counts at each selected desired density, using the gauge's existing calibration constants;
   f. correcting all counts for decay;
   g. correcting all counts for electronic and mechanical changes in the gauge;
   h. calculate densities for all corrected counts;
   i. validate gauge by comparing calculated densities with selected desired densities.

22. A method of re-calibrating a nuclear density gauge comprising
   a. selecting a plurality of desired densities;
   b. providing a nuclear density gauge;
   c. providing a block with a known density;
   d. obtaining counts on the block with a known density;
   e. calculating counts at each selected desired density, using the gauge's existing calibration constants;
   f. correcting all counts for decay;
   g. correcting all counts for electronic and mechanical changes in the gauge;
   h. calculate count ratio by dividing calculated counts by a daily standard count taken on reference block provided with gauge;
   i. re-calibrating the gauge by determining constants A, B and C according to the following equation at each depth using a curve-fitting method $$CR = A\, e^{(-BD)} - C$$

where CR is a ratio of the count on the block of known density and the daily standard count; A, B and C are gauge calibration constants, and D is the material density.

23. The method of claim 22 where the block with a known density is a field block comprising an absorption element which simulates the known density.

24. The method of claim 22, wherein said block with a known density is a reference block of known density and composition.

25. A field-useable instrument for use with a nuclear density gauge comprising an absorption element and an enclosure for holding said absorption element therein, wherein said absorption element is capable of simulating at least one known density when subjected to analysis using the nuclear density gauge, and wherein said enclosure is configured to substantially block radiation emitted by the nuclear density gauge from exiting said enclosure.

26. An instrument for use with a nuclear density gauge comprising an absorption element, wherein said absorption element is capable of simulating a plurality of different densities when subjected to analysis using the nuclear density gauge.

27. A field useable instrument for use with a nuclear density gauge comprising an absorption element and an enclosure for holding said absorption element therein wherein said absorption element is capable of simulating at least one known density when subjected to analysis using the nuclear density gauge, wherein the nuclear density gauge comprises a source rod and a detector and the field instrument further comprises an insertion tube positioned within said enclosure configured to receive the source rod for the purpose of conducting direct transmission nuclear density readings, and wherein said absorption element is translatable into a plurality of positions within said enclosure, and wherein the nuclear density gauge will perceive a corresponding plurality of simulated density readings when said absorption element is placed in said plurality of positions.

28. A field useable instrument for use with a nuclear density gauge comprising an absorption element and an enclosure for holding said absorption element therein wherein said absorption element is capable of simulating at least one known density when subjected to analysis using the nuclear density gauge, wherein the nuclear density gauge comprises a source rod and a detector and the field instrument further comprises an insertion tube positioned within said enclosure configured to receive the source rod for the purpose of conducting direct transmission nuclear density readings, and wherein said absorption element is positioned on said insertion tube, and wherein said insertion tube has a longitudinal depth allowing the source rod of the nuclear density gauge to generate a plurality of readings at increments along said longitudinal depth, and wherein said absorption element simulates at least one density at each of said increment depth positions.

29. A field useable instrument for use with a nuclear density gauge comprising an absorption element and an enclosure for holding said absorption element therein, wherein said absorption element is capable of simulating at least one known density when subjected to analysis using the nuclear density gauge, wherein the nuclear density gauge comprises a source rod and a detector and the field instrument further comprises an insertion tube positioned within said enclosure configured to receive the source rod for the purpose of conducting direct transmission nuclear density readings, and wherein said absorption element increases in thickness along the longitudinal depth of said insertion tube.

30. A field useable instrument for use with a nuclear density gauge comprising an absorption element and an enclosure for holding said absorption element therein, wherein said absorption element is capable of simulating at least one known density when subjected to analysis using the nuclear density gauge, wherein the nuclear density gauge comprises a source rod and a detector and the field instrument further comprises an insertion tube positioned within said enclosure configured to receive the source rod for the purpose of conducting direct transmission nuclear density readings, and wherein said absorption element has a radial thickness and an associated longitudinal length extending between the top and bottom of said absorption element, and wherein said radial thickness increases along said longitudinal length.

31. The field-useable instrument of claim 30, wherein said absorption element is moveable within said enclosure.

32. A field useable instrument for use with a nuclear density gauge comprising an absorption element and an enclosure for holding said absorption element therein, wherein said absorption element is capable of simulating at least one known density when subjected to analysis using the nuclear density gauge, wherein the nuclear density gauge comprises a source rod and a detector and the field instrument further comprises an insertion tube positioned within said enclosure configured to receive the source rod for the purpose of conducting direct transmission nuclear density readings, and wherein said absorption element comprises at least two different materials, a first material and a second material, and wherein said first material is a high density material.

33. A field useable instrument for use with a nuclear density gauge comprising an absorption element and an enclosure for holding said absorption element therein, wherein said absorption element is capable of simulating at least one known density when subjected to analysis using the nuclear density gauge, and wherein the nuclear density gauge includes a radiation source which is longitudinally extendable within said enclosure to desired source depths, and wherein said absorption element represents three different material densities at a single source depth.

34. A method of determining the measurements of a nuclear gauge material measurement device at a field-use site, comprising the steps of:

a. engaging a nuclear gauge having a radiation source capable of emitting radiation and a radiation detector to a nuclear verification device;

b. transmitting radiation from the radiation source into a path defined by the positions of the radiation source, the nuclear gauge verification device, and the radiation detector;

c. positioning a material specimen absorption element configured to simulate a known material density in the radiation path;

d. measuring the radiation emissions generated from said transmitting step received at the radiation detector to establish a nuclear gauge material density reading value;

e. comparing the reading value with a corresponding known material density value associated with the material specimen absorption element, thereby determining the nuclear gauge measurement accuracy; and further comprising the step of translating one or more of the radiation source and the material specimen absorption element in the radiation path from a first position to a second position by one or more of rotating and translating said absorption element in at least one direction from a first reading position to a second reading position relative to the nuclear gauge radiation source.

35. A method of determining the measurements of a nuclear gauge material measurement device at a field-use site, comprising the steps of:
   a. engaging a nuclear gauge having a radiation source capable of emitting radiation and a radiation detector to a nuclear gauge verification device;
   b. transmitting radiation from the radiation source into a radiation path defined by the positions of the radiation source, the nuclear gauge verification device, and the radiation detector;
   c. positioning a material specimen absorption element configured to simulate a known material density in the radiation path;
   d. measuring the radiation emissions generated from said transmitting step received at the radiation detector to establish a nuclear gauge material density reading value; and
   e. comparing the reading value with a corresponding known material density value associated with the material specimen absorption element, thereby determining the nuclear gauge measurement accuracy,
   wherein said method steps (b), (c), (d) and (e) are repeated at multiple longitudinal depths within the verification device to verify measurement accuracy of the nuclear gauge at corresponding selected radiation depths.

36. A method of determining the measurements of a nuclear gauge material measurement device at a field-use site, comprising the steps of:
   a. engaging a nuclear gauge having a radiation source capable of emitting radiation and a radiation detector to a nuclear gauge verification device;
   b. transmitting radiation from the radiation source into a radiation path defined by the positions of the radiation source, the nuclear gauge verification device, and the radiation detector;
   c. positioning a material specimen absorption element configured to simulate a known material density in the radiation path;
   d. measuring the radiation emissions generated from said transmitting step received at the radiation detector to establish a nuclear gauge material density reading value; and
   e. comparing the reading value with a corresponding known material density value associated with the material specimen absorption element, thereby determining the nuclear gauge measurement accuracy,
   wherein said positioning step further includes the step of positioning a material specimen absorption element in the radiation path to simulate a second material density different from the first material density.

37. A method of determining the measurements of a nuclear gauge material measurement device at a field-use site, comprising the steps of:
   a. engaging a nuclear gauge having a radiation source capable of emitting radiation and a radiation detector to a nuclear gauge verification device;
   b. transmitting radiation from the radiation source into a radiation path defined by the positions of the radiation source, the nuclear gauge verification device, and the radiation detector;
   c. positioning a material specimen absorption element configured to simulate a known material density in the radiation path:
   d. measuring the radiation emissions generated from said transmitting step received at the radiation detector to establish a nuclear gauge material density reading value; and
   e. comparing the reading value with a corresponding known material density value associated with the material specimen absorption element, thereby determining the nuclear gauge measurement accuracy,
   wherein said absorption element is sized and configured to represent two different material densities.

38. A method of determining the measurements of a nuclear gauge material measurement device at a field-use site, comprising the steps of:
   a. engaging a nuclear gauge having a radiation source capable of emitting radiation and a radiation detector to a nuclear gauge verification device;
   b. transmitting radiation from the radiation source into a radiation path defined by the positions of the radiation source, the nuclear gauge verification device, and the radiation detector;
   c. positioning a material specimen absorption element configured to simulate a known material density in the radiation path;
   d. measuring the radiation emissions generated from said transmitting step received at the radiation detector to establish a nuclear gauge material density reading value; and
   e. comparing the reading value with a corresponding known material density value associated with the material specimen absorption element thereby, determining the nuclear gauge measurement accuracy, and
   further comprising the step of re-calibrating the nuclear gauge based upon the measured material density value, wherein said re-calibrating step includes the step of determining at least one correction factor associated with one or more of mechanical geometry changes, electronic changes, and nuclear decay.

39. A method of determining the measurements of a nuclear gauge material measurement device at a field-use site, comprising the steps of:
   a. engaging a nuclear gauge having a radiation source capable of emitting radiation and a radiation detector to a nuclear gauge verification device;
   b. transmitting radiation from the radiation source into a radiation path defined by the positions of the radiation source, the nuclear gauge verification device, and the radiation detector;
   c. positioning a material specimen absorption element configured to simulate a known material density in the radiation path;
   d. measuring the radiation emissions generated from said transmitting step received at the radiation detector to establish a nuclear gauge material density reading value; and
   e. comparing the reading value with a corresponding known material density value associated with the material specimen absorption element, thereby determining the nuclear gauge measurement accuracy,
   wherein said engaging step includes positioning the nuclear gauge radiation source and detector on a planar surface of the verification device to verify measurements taken in the backscatter mode.

40. A method of determining the measurements of a nuclear gauge material measurement device at a field-use site, comprising the steps of:
   a. engaging a nuclear gauge having a radiation source capable of emitting radiation and a radiation detector to a nuclear gauge verification device;
   b. transmitting radiation from the radiation source into a radiation path defined by the positions of the radiation source the nuclear gauge verification device, and the radiation detector;

c. positioning a material specimen absorption element configured to simulate a known material density in the radiation path;

d. measuring the radiation emissions generated from said transmitting step received at the radiation detector to establish a nuclear gauge material density reading value; and e. comparing the reading value with a corresponding known material density value associated with the material specimen absorption element, thereby determining the nuclear gauge measurement accuracy, and further comprising the step of re-calibrating the nuclear gauge including establishing three new gauge counts.

41. A method of representing a solid standard reference block for use in a portable field-usable nuclear gauge measurement verification and/or calibration device, comprising the step of:

simulating a standard reference block by sizing and configuring a material specimen absorption element to represent a known material density and absorption value associated with the standard reference block material when operationally engaged with a nuclear gauge, wherein said simulating step includes one or more of configuring, positioning, and translating said absorption element in a measurement device to represent a plurality of different standard reference block materials when engaged with a nuclear gauge having a radiation source and detector.

42. A method of representing a solid standard reference block for use in a portable field-usable nuclear gauge measurement verification and/or calibration device, comprising the step of:

simulating a standard reference block by sizing and configuring a material specimen absorption element to represent a known material density and absorption value associated with the standard reference block material when operationally engaged with a nuclear gauge, wherein said simulating step includes one or more of configuring, positioning, and translating said absorption element in a measurement device to represent a plurality of different standard reference block materials when engaged with a nuclear gauge having a radiation source and detector, and wherein said source can be manipulated into different source depths in the field useable device, and wherein said representation of a plurality of different standard reference block materials includes representing at least three different material densities at a single source depth.

43. A method of representing a solid standard reference block for use in a portable field-usable nuclear gauge measurement verification and/or calibration device, comprising the step of:

simulating a standard reference block by sizing and configuring a material specimen absorption element to represent a known material density and absorption value associated with the standard reference block material when operationally engaged with a nuclear gauge, wherein said simulating step includes one or more of configuring, positioning, and translating said absorption element in a measurement device to represent a plurality of different standard reference block materials when engaged with a nuclear gauge having a radiation source and detector, and, wherein said source can be manipulated into different source depths in the field useable device, and wherein said simulating step includes simulating a plurality of different standard reference block material densities at a plurality of source depths.

* * * * *

UNITED STATES PATENT AND TRADEMARK OFFICE
CERTIFICATE OF CORRECTION

PATENT NO. : 5,923,726
DATED : July 13, 1999
INVENTOR(S) : Regimand

It is certified that error appears in the above-indentified patent and that said Letters Patent is hereby corrected as shown below:

On the Title Page

In line 3 of the Abstract, please insert - - the - - after "where" and before "absorption".

In the Specification:

Column 8, line 30, please move --geometry of the absorption element within the -- in front of "radiation path". Line 30 should then read --geometry of the absorption element within the radiation path--

Column 8; line 31, please delete "path".

Column 15, line 4, please move --Eij (Step 320)-- to the end of line 3 after "Densities".

In the Claims:

Column 17, line 63, please insert - - , - - after "15" and before "wherein".

Column 19, line 2, please delete "Care" and insert - - C are --.

Column 19, line 24, please insert - - , - - after "therein".

Column 19, line 39, please insert - - , - - after "therein".

Column 22, line 26, please insert - - , - - before "thereby" and delete "," after "thereby".

Column 23, line 1, please insert - - , - - after "source".

Signed and Sealed this

Twenty-second Day of May, 2001

Attest:

NICHOLAS P. GODICI

Attesting Officer     Acting Director of the United States Patent and Trademark Office